United States Patent [19]

Liersch et al.

[11] Patent Number: 5,422,249
[45] Date of Patent: Jun. 6, 1995

[54] PROCESS FOR THE MANUFACTURE OF THROMBIN INHIBITORS

[75] Inventors: Manfred Liersch; Hans Rink, both of Riehen; Walter Märki, Möhlin; Markus G. Grütter, Hochwald; Bernd Meyhack, Magden, all of Switzerland

[73] Assignees: Ciba-Geigy Corporation, Ardsley, N.Y.; UCP Gen-Pharma AG, Kirchberg, Switzerland

[21] Appl. No.: 121,974

[22] Filed: Sep. 15, 1993

Related U.S. Application Data

[63] Continuation of Ser. No. 700,997, May 10, 1991, abandoned, which is a continuation of Ser. No. 582,816, Sep. 13, 1990, abandoned, which is a continuation of Ser. No. 211,065, Jun. 20, 1988, abandoned, which is a continuation of Ser. No. 744,453, Jun. 13, 1985, abandoned.

[30] Foreign Application Priority Data

Jun. 14, 1984 [CH] Switzerland ............... 2882/84

[51] Int. Cl.[6] .............. C12N 15/15; C12N 15/70
[52] U.S. Cl. .................. 435/69.2; 435/172.3; 435/252.33; 435/320.1; 536/23.5
[58] Field of Search .......... 435/69.2, 172.1, 172.2, 435/172.3, 320.1, 252.3, 252.33; 536/23.5

[56] References Cited

U.S. PATENT DOCUMENTS

| | | | |
|---|---|---|---|
| 3,432,596 | 3/1969 | Markwardt et al. | 424/520 |
| 4,517,294 | 5/1985 | Bock et al. | 435/70 |
| 4,654,302 | 3/1987 | Fritz et al. | 435/70 |
| 4,704,362 | 11/1987 | Itakura et al. | 435/252.3 |

FOREIGN PATENT DOCUMENTS

| | | |
|---|---|---|
| 0114506 | 8/1984 | European Pat. Off. ..... C12N 15/00 |
| 0158564 | 10/1985 | European Pat. Off. ..... C12N 15/00 |
| 0158986 | 10/1985 | European Pat. Off. ..... C07K 7/10 |
| 3342139 | 6/1985 | Germany . |
| 84/9068 | 7/1985 | South Africa . |

OTHER PUBLICATIONS

Winkler, et al., Biotechnology, 3, 990–1000 (1985).
Schoemaker, et al., Embo-J. 4, 775–780 (1985).
Miyanohara, et al., Prod. Natl. Acad. Sci. USA 80, 1–5 (1983).
Maniatis et al. 1982, Molecular Cloning: A Laboratory Manual, Cold Spring Harbor Laboratory, pp. 226–227, 404 & 412–413 and 422.
Grosjean et al. Gene 18:199–209 (1982).
Vogt et al. J. Biol. Chem. 245:4760–4769 (1970).
Valenzuela et al. Nature 298:347–350 (1982).
Palua et al. Gene 22:229–235 (1983).
Bergman et al. Biol. Chem. Hoppe Seyler's 367:731–740 (1986).
Miller, p. 687, In *E. coli* and *S. typhimurium*, Cell. and Mol. Biol. Ed. Chief Neidhardt, ASM, Wash. D.C. (1987).
Chang, FEBS 1044, 164, pp. 307–313 (1983).
Williams, et al., Science, 215, 687–685 (1986).
Wetzel et al., In "The Peptides", vol. 5, Eds. Cross et al., Academic Press, N.Y., 1983, p. 32.

(List continued on next page.)

Primary Examiner—Jacqueline Stone
Assistant Examiner—J. LeGuyader
Attorney, Agent, or Firm—James Scott Elmer

[57] ABSTRACT

The invention relates to DNA sequences that code for the amino acid sequence of the thrombin inhibitor hirudin, hybrid vectors containing such DNA sequences, host cells transformed with such hybrid vectors, novel polypeptides with thrombin-inhibiting activity produced from such transformed host cells, processes for the manufacture of these DNA sequences, hybrid vectors and transformed host cells, and processes for the manufacture of these thrombin-inhibitors using the transformed host cells. The hirudin compounds that can be produced according to the invention have valuable pharmacological properties.

7 Claims, 4 Drawing Sheets

OTHER PUBLICATIONS

Gueriguian et al. eds, "Insulines, Growth Hormone and Recombinant DNA Technology", Lavan Press, N.Y., 1981, p. 39.
Winnacher, "From Genes to Clones: Introduction to Gene Technology", WCH Publishers, N.Y., 1987, p. 293.
Seeburg et al., DNA, vol. 2, pp. 37–45 (1983).
Guarente, et al., Science, vol. 209, pp. 1428–1430 (1980).
Thrombosis Research 2, 229–238 (1973) (Bagdy et al).
Methods Enzym., vol. XLV (1976) 669–678 (Bagdy et al).
Thromb. Haemostasis 47, 226–229 (1982) (Markwardt et al).
Die Pharmazie 36, 653–660 (1981) (Walsmann et al).
FEBS Letters 165, 180–184 (1984) (Dodt et al).

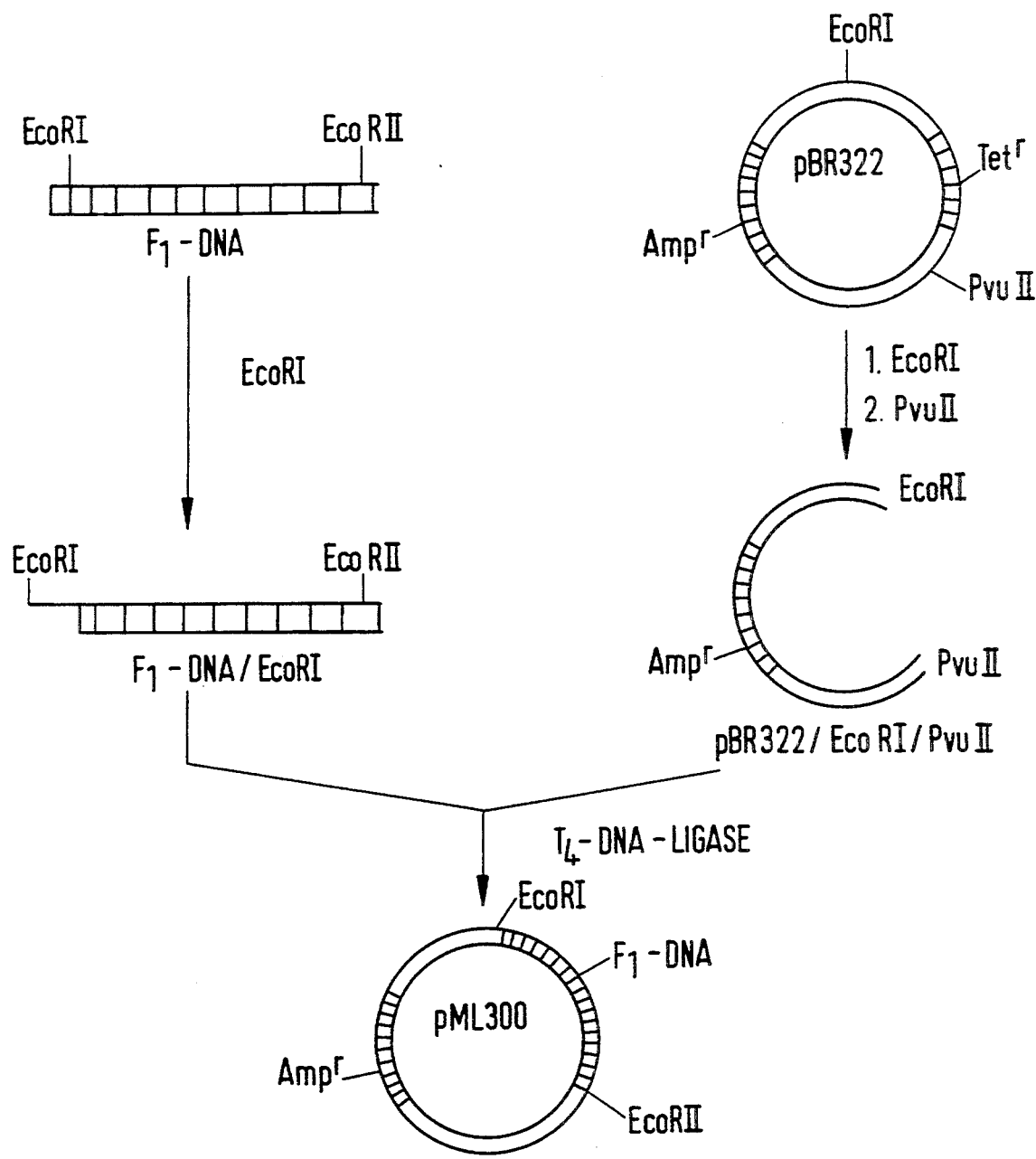
Fig. 1  CONSTRUCTION OF PLASMID pML300

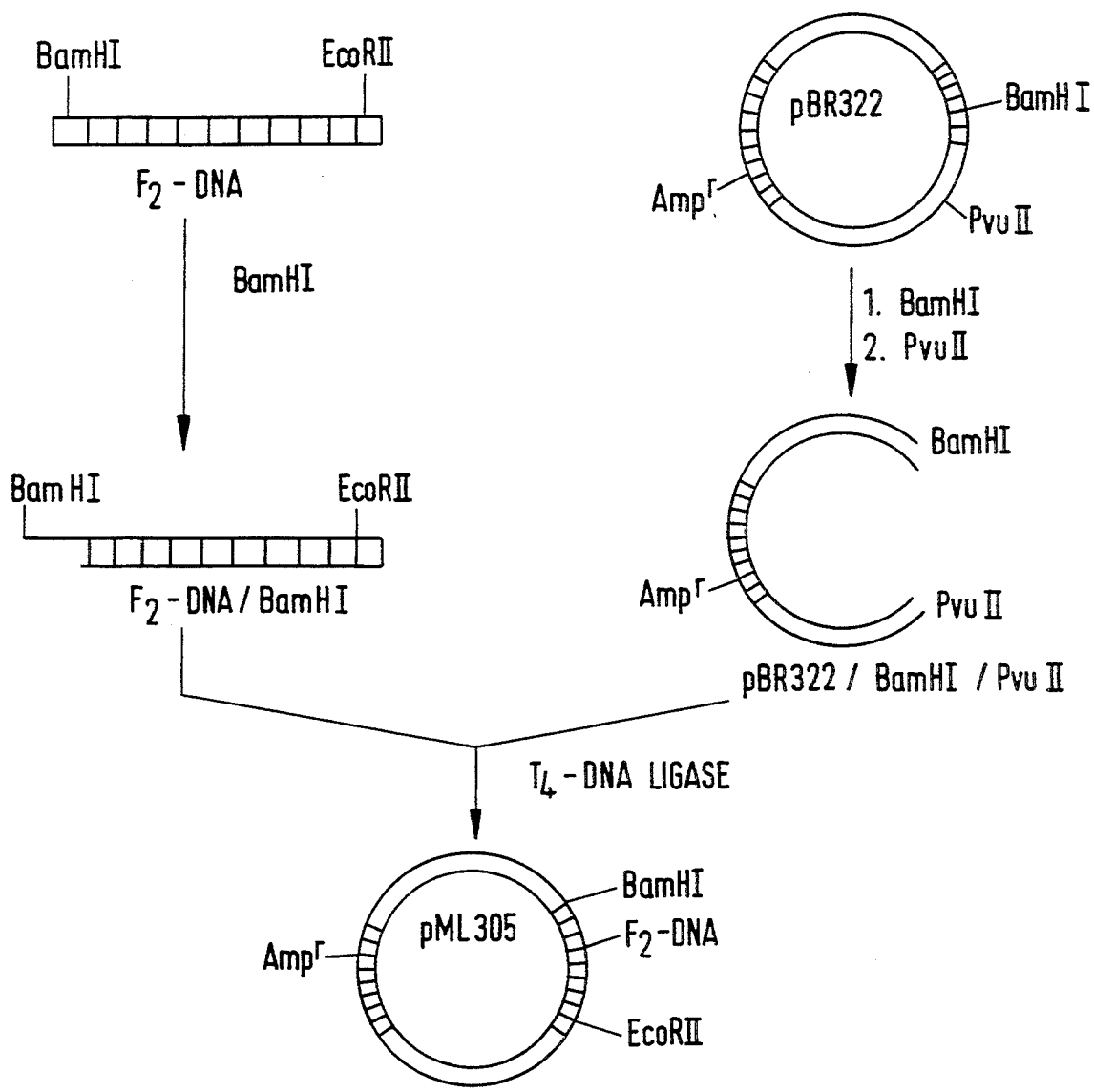
Fig. 2  CONSTRUCTION OF PLASMID pML305

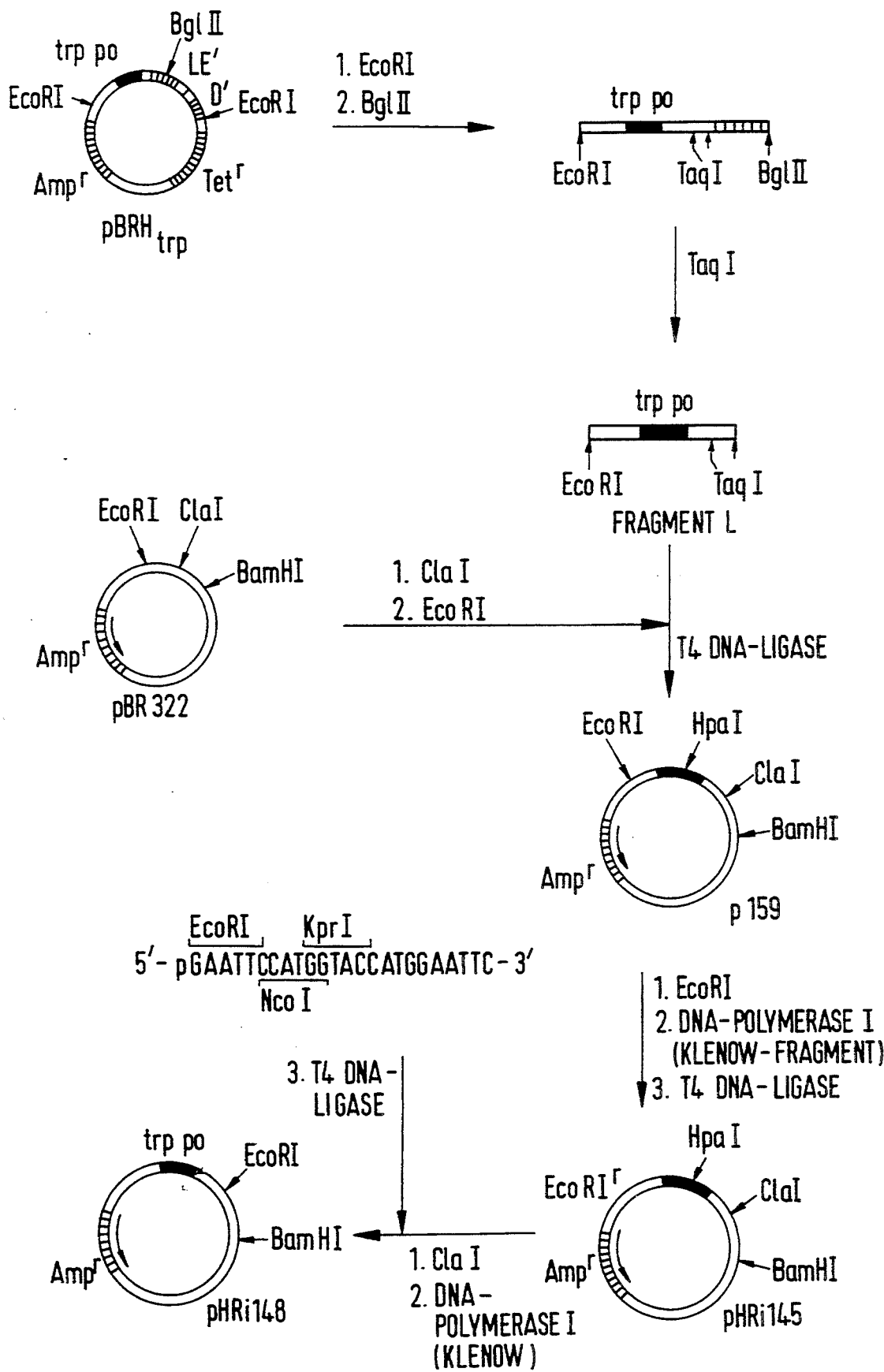
Fig. 3  CONSTRUCTION OF PLASMID pHRi148

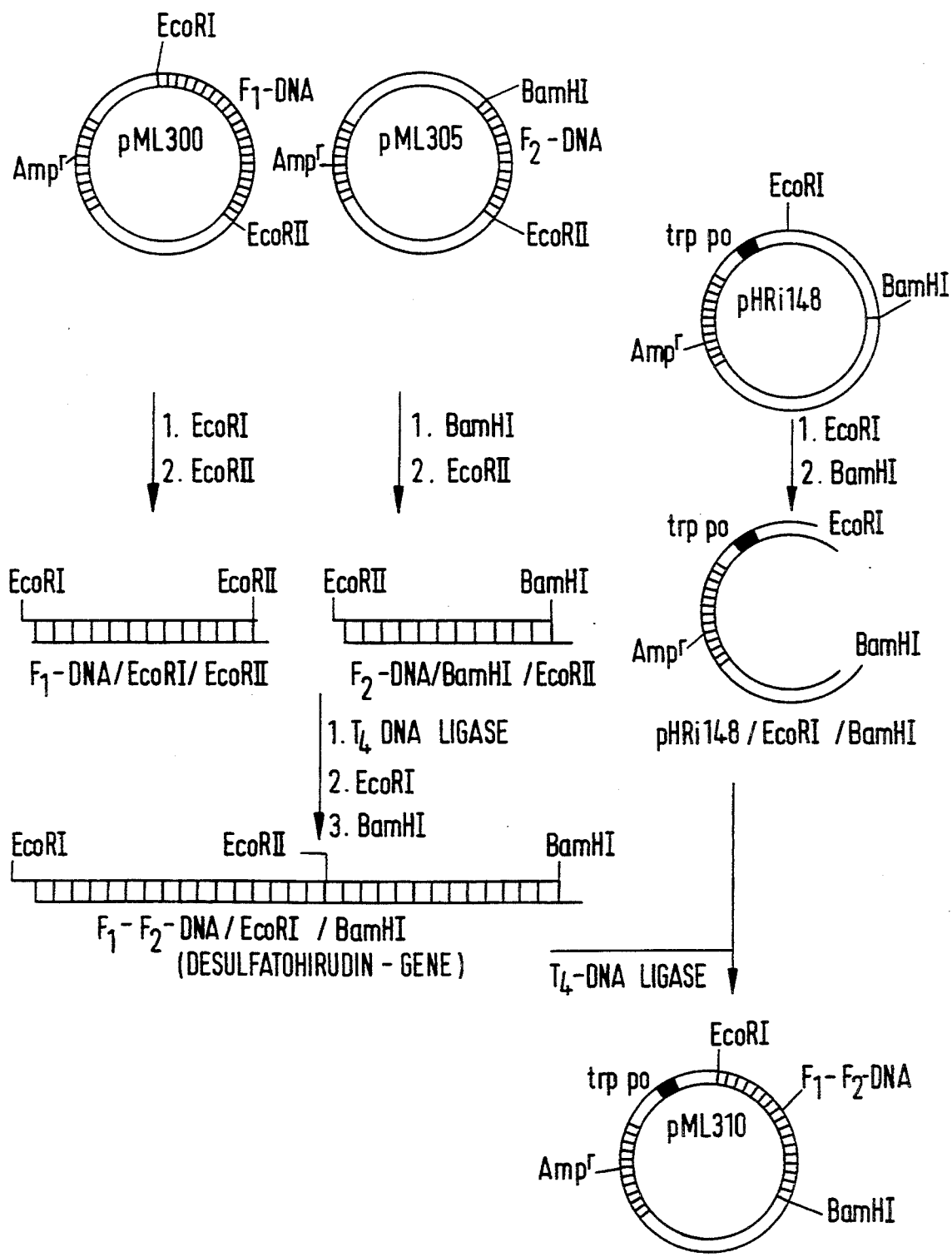

PROCESS FOR THE MANUFACTURE OF THROMBIN INHIBITORS

This application is a continuation of application Ser. No. 07/700,997, filed May 10, 1991, now abandoned, which is a continuation of application Ser. No. 582,816, filed Sep. 13, 1990 now abandoned, which is a continuation of application Ser. No. 211,065, filed Jun. 20, 1988, now abandoned, which is a continuation of application Ser. No. 744,453, filed Jun. 13, 1985, now abandoned.

The invention relates to DNA sequences that code for the amino acid sequence of the thrombin inhibitor hirudin, hybrid vectors containing such DNA sequences, host cells transformed with such hybrid vectors, novel polypeptides with thrombin-inhibiting activity produced from such transformed host cells, processes for the manufacture of these DNA sequences, hybrid vectors and transformed host cells, and processes for the manufacture of these thrombin inhibitors using the transformed host cells.

In the plasma of a healthy mammalian organism a dynamic equilibrium exists between the fibrinolytic system and the coagulation system, as a result of which an efficiently operating vascular network is maintained. When vascular lesions occur, the coagulation system deposits a fibrin matrix which, after achieving the haemostatic condition, is broken down again by the fibrinolytic system. In cases in which the fibrinolytic potential of the organism is not sufficient to break down intravascular thrombi that have been formed, for example in patients who suffer from thrombo-embolisms or postoperative complications, supporting the organism by the administration of thrombolytic agents or anticoagulants proves indispensable.

In conventional anticoagulation therapy especially heparin, but also 4-hydroxycumarin derivatives and 1,3-indanedione derivatives, have been used hitherto. Although notable success has been achieved with these agents they nevertheless have some disadvantages. For example, heparin does not act directly on the blood coagulation process but demonstrates its coagulation-inhibiting action indirectly by accelerating the inhibition of thrombin and factor X by antithrombin III. Heparin furthermore enters into numerous non-specific reactions in the organism and is neutralised by platelet factor 4, which prejudices its use especially in consumption coagulopathy and disseminated intravascular coagulation (DIC). There is therefore a need for alternative and more specific agents for anticoagulation therapy.

An anticoagulant that occurs naturally in leeches (Hirudo medicinalis), hirudin, has been known for a long time. Hirudin is a polypeptide consisting of 65 amino acids with a completely determined primary structure (1) and has as structural characteristics an accumulation of hydrophobic amino acids at the N-terminus and of polar amino acids at the C-terminus, a tyrosine residue (Tyr$^{63}$) present as sulphate monoester, and three disulphide bridges of which the exact arrangement is, however, not yet known.

Hirudin, with a $K_i$-value (complex dissociation constant) of $6 \times 10^{-11}$M, is the strongest thrombin inhibitor known and is characterised by a specific affinity to thrombin; other enzymes of the blood coagulation cascade are not inhibited by hirudin. In contrast to heparin, hirudin exerts its inhibiting action directly on thrombin and, unlike the former, does not act through antithrombin III. The only pharmacologically detectable effect of purified hirudin is the inhibition of blood coagulation and the prophylaxis of thrombosis. No effect on heart rate, respiration, blood pressure, thrombocyte count, fibrinogen and haemoglobin could be observed when administered intravenously to dogs, even in high doses. In tests on rats, pigs and dogs, hirudin has proved effective in experimental thrombosis (induced either by stasis or by the injection of thrombin), in endotoxin shock, and also in DIC (disseminated intravascular coagulation). Whenever direct comparison tests have been carried out, hirudin has proved to be superior to heparin.

Although long known, hirudin has not as yet achieved the broad therapeutic use that might be expected on the basis of its excellent biological properties. Its extremely limited availability is a serious drawback which stands in the why of its widespread use in medicine. Up until now, hirudin preparations have been obtainable exclusively from natural material, which is expensive and difficult to obtain, using leech extracts, and employing time-consuming and costly isolation and purification processes (cf. ref. 2). The relatively long sequence of 65 amino acids has meant that, for economic reasons, also the conventional peptide synthesis offers little hope of success. New methods must therefore be applied for the manufacture of adequate amounts of hirudin that render possible detailed clinical tests of its therapeutic potential and its broad therapeutic use in anticoagulation therapy.

Such methods are offered especially by recombinant DNA technology. By means of this technology it is possible to manufacture the most varied physiologically active polypeptides by the cultivation of correspondingly genetically modified microorganisms or mammalian cell cultures.

The problem underlying the present invention is accordingly, with the aid of genetic technology techniques, to provide an expression system that permits the microbiological manufacture on an industrial scale of polypeptides with hirudin activity. This problem is solved in the present invention by the preparation of hybrid plasmids that contain a DNA sequence coding for the amino acid sequence of hirudin, which DNA sequence is controlled by an expression control sequence in such a manner that, in a host cell transformed with these hybrid vectors, polypeptides with hirudin activity are expressed.

It was to be expected that the expression of such DNA sequences in transformed host cells (with the exception of transformed leech cells), in the absence of an additionally incorporated sulphate-transferring enzyme system, would result in a product that would differ from natural hirudin essentially by the absence of the sulphate radical at the tyrosine-63 residue. The biological function of the sulphate radical in proteins in general, and in hirudin in particular, has not been definitively clarified in detail, but the sulphate radical, in accordance with current knowledge, is said to have a not unimportant influence on the physiological properties of the protein. The sulphate radical is thus said to have the following functions:

(1) positive influence on the biological activity of the protein;
(2) participation in regulatory cell processes (as known in the case of reversible phosphorylation);
(3) stimulation of secretion, that is to say the sulphated moiety acts as a marker for recognition as a secretory protein: all known sulphated proteins are secretory or transmembranal proteins.

Surprisingly, it has now been found that, contrary to theoretical ideas, the valuable biological properties of hirudin are retained even if the characteristic sulphate monoester group is removed from the phenolic hydroxy of the Tyr$^{63}$ residue. The hirudin compounds without the sulphate radical (desulphatohirudins) produced by means of the transformed microorganisms according to the invention have, by comparison with natural hirudin, proved in their biological properties, especially in their anticoagulative activity, to be qualitatively and quantitatively at least equivalent.

In the following there are to be understood by DNA sequences or genes that code for the amino acid sequence of hirudin those DNA sequences or genes which on expression produce hirudin-like polypeptides that differ from natural hirudin especially by the absence of the sulphate ester group at the tyrosine-63 residue (desulphatohirudins).

Manufacture of DNA sequences that code for the amino acid sequence of hirudin

The invention relates to DNA sequences that code for the amino acid sequence of hirudin, and to fragments thereof.

The invention further relates to processes for the manufacture of DNA sequences that code for the amino acid sequence of hirudin, and the manufacture of fragments thereof, characterised in that the hirudin structural gene is isolated from genomic leech DNA, or a complementary double-stranded hirudin DNA (hirudin-ds cDNA) is produced from hirudin mRNA, or a gene coding for the amino acid sequence of hirudin, or fragments thereof, is (are) produced by means of chemical and enzymatic processes.

Genomic hirudin DNA and hirudin-ds cDNA are obtained, for example, according to methods that are known per se. For example, genomic hirudin DNA is obtained, for example, from a leech gene bank that contains the hirudin gene by cloning the leech DNA fragments in a microorganism and identifying clones that contain hirudin DNA, for example by colony hybridisation using a radioactively labelled, hirudin DNA-specific oligodeoxynucleotide that contains at least 15, and preferably from 15 to 30, deoxynucleotides. The resulting DNA fragments as a rule contain in addition to the hirudin gene other undesired DNA constituents that can be removed by treatment with suitable exo- or endo-nucleases.

Double-stranded hirudin cDNA can be produced, for example, by obtaining mRNA from suitable leech cells, which are preferably induced to form hirudin, enriching the hirudin-mRNA in the resulting mRNA mixture in a manner known per se, using this mRNA as a template for the preparation of single-stranded cDNA, synthesising from this, by means of an RNA-dependent DNA polymerase, ds cDNA, and cloning the latter into a suitable vector. Clones that contain hirudin cDNA are identified, for example in the manner described above, by colony hybridisation using a radioactively labelled, hirudin DNA-specific oligodeoxynucleotide.

The genomic hirudin DNA obtained in this manner or the hirudin cDNA is linked preferably at the 5' and at the 3'-end with chemically synthesised adapter oligodeoxynucleotides that contain the recognition sequence for one or various restriction endonuclease(s) and thus facilitate insertion into suitable vectors. In addition, the adapter molecule for the 5'-end of the hirudin DNA or cDNA must also contain the translation start signal (ATG). The translation start signal must be so arranged that the codon for the first amino acid of hirudin directly follows it.

Since the structure of the natural hirudin gene is not known and the chemical synthesis of a gene (desulphatohirudin gene) coding for the amino acid sequence of hirudin, owing to modern synthesising methods, offers advantages especially from the point of view of time, chemical synthesis is a preferred embodiment of the present invention.

Chemical synthesis of a desolphatohirudin gene

The invention relates especially to a process for the manufacture of a structural gene for desulphatohirudin or fragments thereof which is characterised in that segments of the coding and of the complementary strand of the desulphatohirudin gene are chemically synthesised and resulting segments are converted enzymatically into a structural gene of desulphatohirudin or into fragments thereof.

The invention further relates to double-stranded DNAs that code for desulphatohirudin.

The DNAs according to the invention contain, in addition to the codons for desulphatohirudin, translation start and stop signals that render possible expression in suitable host cells, for example E. coli, and also nucleotide sequences at the ends which are suitable for insertion into a vector.

In a preferred embodiment of the invention, the DNA includes at the 5'-end a nucleotide sequence that can be cleaved by a restriction enzyme, followed by the translation start signal, codons for the amino acids of hirudin, which render possible cleavage optionally at one or more sites by a restriction enzyme, a translation stop signal and, at the 3'-end, a nucleotide sequence that can be cleaved by a restriction enzyme. Restriction enzymes that can be used in accordance with the invention are, for example, EcoRI, EcoRII, BamHI, HpaII, PstI, HinfI or HindIII.

The invention relates especially to a double-stranded DNA consisting of a nucleotide sequence of the formula I and the complementary nucleotide sequence

| 5'(X')$_n$ | Met ATG | | | | | | |
|---|---|---|---|---|---|---|---|
| Val | Val | Tyr | Thr | Asp | Cys | Thr | Glu |
| GTX | GTX | TAY | ACX | GAY | TGY | ACX | GAM |
| Ser | Gly | Gln | Asn | Leu | Cys | Leu | CYS |
| QRS | GGX | CAM | AAY | YTZ | TGY | YTZ | TGY |
| Glu | Gly | Ser | Asn | Val | Cys | Gly | Gln |
| GAM | CGX | QRS | AAY | GTX | TGY | GGX | CAM |
| Gly | Asn | Lys | Cys | Ile | Leu | Gly | Ser |
| GGX | AAY | AAM | TGY | ATN | YTZ | GGX | QRS |
| Asp | Gly | Glu | Lys | Asn | Gln | Cys | Val |
| GAY | GGX | GAM | AAM | AAY | CAM | TGY | GTX |
| Thr | Gly | Glu | Gly | Thr | Pro | Lys | Pro |
| ACX | GGX | GAM | GGX | ACX | CCX | AAM | CCX |

-continued

| Gln | Ser | His | Asn | Asp | Gly | Asp | Phe |
|-----|-----|-----|-----|-----|-----|-----|-----|
| CAM | QRS | CAY | AAY | GAY | GGX | GAY | TTY |
| Glu | Glu | Ile | Pro | Glu | Glu | Tyr | Leu |
| GAM | GAM | ATN | CCX | GAM | GAM | TAY | YTZ |
| Gln | NON | | | | | | |
| CAM | TMK | (X')$_m$ 3' | | | | | |

(I)

in which the nucleotide sequence is represented commencing with the 5'-end and, for the purpose of better understanding, the amino acids for which each triplet codes are indicated, and in which the symbols have the following meanings:

A = deoxyadenosyl,
T = thymidyl,
G = deoxyguanosyl,
C = deoxycytidyl,
X = A, T, C or G,
Y = T or C,
Z = A, T, C or G when Y = C, or
Z = A or G when Y = T,
Q = T or A,
R = C and S = A, T, C or G when Q = T, or
R = G and S = T or C when Q = A,
M = A or G,
L = A or C,
N = T, C or A,
K = A or G when M = A, or
K = A when M = G,

| for glycine (Gly) | GGT |
|---|---|
| cysteine (Cys) | TGC |
| valine (Val) | GTT |
| leucine (Leu) | CTG |
| serine (Ser) | TCT |
| threonine (Thr) | ACC |
| phenylalanine (Phe) | TTC |
| tyrosine (Tyr) | TAC |
| methionine (Met) | ATG |
| aspartic acid (Asp) | GAC |
| glutamic acid (Glu) | GAA |
| lysine (Lys) | AAA |
| isoleucine (Ile) | ATC |
| histidine (His) | CAC |
| proline (Pro) | CCG |
| glutamine (Gln) | CAG |
| asparagine (Asn) | AAC |

The preferred stop signal (NON) is the codon TAG.

A preferred embodiment of a gene coding for the amino acid sequence of hirudin in the above-described manner is the DNA of the formula II,

```
         Met Val Val Tyr Thr Asp Cys Thr Glu Ser Gly Gln Asn Leu Cys Leu Cys Glu Gly
    CTGGAATTCATGGTTGTTTACACCGACTGCACCGAATCTGGTCAGAACCTGTGCCTGTGCGAAGGT
    GACCTTAAGTACCAACAAATGTGGCTGACGTGGCTTAGACCAGTCTTGGACACGGACACGCTTCCA
        (EcoRI)

Ser Asn Val Cys Gly Gln Gly Asn Lys Cys Ile Leu Gly Ser Asp Gly Glu Lys Asn Gln Cys Val
TCTAACGTTTGCGGTCAGGGTAACAAATGCATCCTGGGTTCTGACGGTGAAAAAAACCAGTGCGTT
AGATTGCAAACGCCAGTCCCATTGTTTACGTAGGACCCAAGACTGCCACTTTTTTTGGTCACGCAA
                                        (EcoRI)

Thr Gly Glu Gly Thr Pro Lys Pro Gln Ser His Asn Asp Gly Asp Phe Glu Glu Ile Pro Glu Glu
ACCGGTGAAGGTACCCCGAAACCGCAGTCTCACAACGACGCTGACTTCGAAGAAATCCCGGAAGAA
TGGCCACTTCCATGGGGCTTTGGCGTCAGAGTGTTGCTGCCACTGAAGCTTCTTTAGGGCCTTCTT

Tyr Leu Gln NON
TACCTGCAGTAGGATCCTG
ATGGACGTCATCCTAGGAC
              (BamHI)
```
(II)

and (X')$_n$ and (X')$_m$ represent nucleotide sequences with n and m being more than 3 and less than 100, especially more than 5 and less than 15, which may be recognised and cleaved by a restriction enzyme.

In a preferred embodiment, the DNA sequence contains at the 5'-end a nucleotide sequence that can be cleaved by EcoRI, in the middle a nucleotide sequence that can be cleaved by EcoRII and at the 3'-end a nucleotide sequence that can be cleaved by BamHI.

The invention includes especially a double-stranded DNA that contains triplets that are preferred by *E. coli* and code for the amino acids of hirudin. Such triplets are especially:

in which A, T, G and C have the meanings given under formula I and, for the purpose of better understanding, the amino acids for which each triplet codes and the cleavage sites for the restriction enzymes are indicated.

The invention also includes fragments of a DNA that codes for desulphatohirudin.

In particular the invention includes double-stranded DNA fragments of the desulphatohirudin gene, especially those of which the ends may be cleaved by restriction enzymes. Such double-stranded DNA fragments of the hirudin gene have especially from 30 to 70 base pairs.

For example, the invention includes DNA fragments of the formula III (F$_1$) and of the formula IV (F$^2$):

```
         Met Val Val Tyr Thr Asp Cys Thr Glu Ser Gly Gln Asn Leu Cys Leu Cys Glu Gly
    CTGGAATTCATGGTTGTTTACACCGACTGCACCGAATCTGGTCAGAACCTGTGCCTGTGCGAAGGT
    GACCTTAAGTACCAACAAATGTGGCTGACGTGGCTTAGACCAGTCTTGGACACGGACACGCTTCCA
        (EcoRI)

Ser Asn Val Cys Gly Gln Gly Asn Lys Cys Ile Leu Gly Ser
TCTAACGTTTGCGGTCAGGGTAACAAATGCATCCTGGGTTCTG
```

-continued
```
AGATTGCAAACGCCAGTCCCATTGTTTACGTAGGACCCAAGAC
                                 (EcoRI)
```
F₁ (III)

```
  Ile Leu Gly Ser Asp Gly Glu Lys Asn Gln Cys Val Thr Gly Glu Gly Thr Pro Lys Pro
CATCCTGGGTTCTGACGGTGAAAAAACCAGTGCGTTACCGGTGAAGGTACCCCGAAACCG
GTAGGACCCAAGACTGCCACTTTTTTGGTCACGCAATGGCCACTTCCATGGGGCTTTGGC
  (EcoRI)

Gln Ser His Asn Asp Gly Asp Phe Glu Glu Ile Pro Glu Glu Tyr Leu Gln NON
CAGTCTCACAACGACGCTGACTTCGAAGAAATCCCGGAAGAATACCTGCAGTAGGATCCTG
GTCAGAGTGTTGCTGCCACTGAAGCTTCTTTAGGGCCTTCTTATGGACGTCATCCTAGGAC
                                                          (BamHI)
```
F₂ (IV)

The invention also includes single-stranded DNA fragments of the desulphatohirudin gene, especially those that can be joined by chemical and/or enzymatic methods to form the desulphatohirudin gene. The invention relates especially to single-stranded DNA fragments having more than twenty nucleotides, especially having from 20 to 70 nucleotides.

Preferably the invention relates to the single-stranded and double-stranded DNA fragments described in the Examples.

Methods of synthesising DNA have been summarised by S. A. Narang (3). The known synthesising techniques permit the manufacture of polynucleotides having a length of towards 20 bases in a good yield, high purity and in a relatively short time. Suitably protected nucleotides are linked with one another by the phosphodiester method (4) or the even more efficient phosphotriester method (5) or phosphite triester method (6). Simplification of the synthesis of oligo- and polynucleotides is rendered possible by the solid phase method in which the nucleotide chains are bonded to a suitable polymer. Itakura et al. (7) use in solid phase synthesis instead of individual nucleotides trinucleotides linked by the phosphotriester method, which can then be condensed within a short time and in good yields, for example to form a polynucleotide with 31 bases. The authentic double-stranded DNA can be built up enzymatically from chemically produced short segments. Khorana et al. (8) use for this purpose overlapping polynucleotide sequences from both DNA strands, which are held together in the correct arrangements by base pairing and are then chemically linked by the enzyme DNA ligase. A further possibility comprises incubating one polynucleotide sequence from each of the two DNA strands having a short overlapping segment, in the presence of the four required deoxynucleoside triphosphates, with a DNA polymerase, for example DNA polymerase I, Klenow fragment of polymerase I, T₄ DNA polymerase, or with AMV (avian myeloblastosis virus) reverse transcriptase. In this process the two polynucleotide sequences are held together in the correct arrangement by base pairing and supplemented by the enzyme with the required nucleotides to form a complete double-stranded DNA (9). Itakura et al. (10) describe how, based on this principle, a 132 base pair-long segment of the human leucocyte interferon α₂-gene can be built up in the presence of DNA-polymerase I (Klenow fragment) from 4 chemically synthesised fragments having a length of from 39 to 42 bases, achieving a 40% saving of chemical synthesis by comparison with the above-described method in which only ligase is used.

The present invention relates to a process for the manufacture of DNAs that contain a structural gene of desulphatohirudin and are suitable for expression in host cells, and the ends of which render possible insertion into vectors, and to the manufacture of fragments thereof, characterised in that a) a suitably protected deoxynucleoside is bonded to a solid carrier, b) suitably protected di-, tri- or tetra-nucleotides are manufactured according to the phosphotriester or phosphite method, c) a deoxynucleoside or oligodeoxynucleotide bonded to the carrier is linked with suitably protected mono-nucleotides or di-, tri- or tetra-nucleotides (produced according to b)) in accordance with the phosphotriester or the phosphite method, d) oligodeoxynucleotides obtainable according to c) which are bonded to carriers and have a length of from approximately 20 to approximately 70 bases are removed from the carrier, if desired purified, freed of protecting groups, and the free 5'-terminal hydroxy groups are phosphorylated, e1) 2 oligodeoxynucleotides each of a length of from approximately 20 to approximately 70 bases from the coding and from the complementary strand having at least 3, and preferably from 8 to 15, overlapping base pairs are annealed and are supplemented with a DNA polymerase in the presence of the four deoxynucleoside triphosphates to form double-stranded DNA segments (fragments of the desulphatohirudin gene), and, optionally, 2 double-stranded DNA segments with suitable ends phosphorylated in accordance with d) are linked using a ligase to form the desulphatohirudin structural gene, or 2 resulting double-stranded DNA segments are subcloned into suitable vectors, then phosphorylated in accordance with d) and linked using a ligase to form the desulphatohirudin structural gene, or e2) each 2 oligodeoxynucleotides alternately originating from the coding and from the complementary strand having a length of, for example, from 20 to 70 bases and each having at least 3, and preferably from 8 to 15, overlapping base pairs, are annealed, made up with a DNA polymerase in the presence of the four deoxynucleoside triphosphates, and linked using ligase to form the desulphatohirudin structural gene.

The process according to the invention is known per se, but only by suitable combination of the conditions and substantial improvements according to the invention does it render possible the manufacture of DNAs coding for the amino acid sequence of hirudin.

A plurality of solid carrier materials can be used in step a), such as polystyrene of various cross-linkages and swelling properties, polyacrylamides, polyacrylamide copolymers, polyamides supported on inorganic material such as kieselguhr, silica gel or Alox, or functionalised silanes. In a preferred embodiment of the invention the solid carrier materials used are crosslinked polystyrenes, which are linked in a manner known per se with the 5'-OH group of suitably protected deoxynucleosides by way of "spacers", such as alkylene groups having from 2 to 12 carbon atoms interrupted by from 1 to 5 polar divalent functional groups, such as imino, oxo, thio, oxycarbonyl or amidocarbonyl. Especially preferred is the reaction with succinic acid anhydride of nucleosides of the formula V protected in the 5'-position and optionally in the base moiety, in which $R^1$ represents a protecting group that can be removed by acid, such as a triarylmethyl protecting group, for example a 4-methoxytrityl group or a 4,4'-dimethoxytrityl group, or a tri-lower alkylsilyl protecting group, for example a tert.-butyldimethylsilyl group, and in which B represents an optionally protected base selected from the group comprising thymyl, cytosyl, adenyl and guanyl, optionally in the presence of bases, such as pyridine, triethylamine or dimethylaminopyridine, followed by reaction with aminomethylated polystyrene that is crosslinked by from 0.5 to 2% divinylbenzene, with the aid of reagents that activate the carboxylic acid radical, preferably N-hydroxy succinimide, or p-nitrophenol and dehydrating agents, such as carbodiimides, for example dicyclohexyl carbodiimide (scheme 1).

The reaction is carried out in an inert aprotic solvent, for example pyridine, tetrahydrofuran, dioxan, ethyl acetate, chloroform, methylene chloride, dimethylformamide or diethyl acetamide, or in mixtures thereof, at room temperature or at slightly elevated or reduced temperature, for example in a temperature range of from approximately $-10°$ C. to approximately 50° C., preferably at room temperature, it being possible for the reaction in the presence of a dehydrating agent also to be carried out at a lower temperature, for example at approximately 0° C.

reacted, optionally in the presence of dehydrating agents or in the presence of bases, with activating phosphoric esters of the formula VII, in which each of $x^1$ and $X^2$, independently of the other, represents hydroxy or a salt derived therefrom, halogen, imidazolyl, 1,2,4-triazol-1-yl, tetrazolyl or 1-benztriazolyloxy, and $X^2$ in addition also represents 2-cyanoethoxy, 2-trihaloethoxy, 2-arylsulphonylethoxy, 2-lower alkylthioethoxy, 2-arylthioethoxy or 2-(4-nitrophenyl) ethoxy, and $R^2$ represents a protecting group that can be removed by a base or by a nucleophilic compound, such as by ammonium hydroxide, thiophenolate or by an aryl aldoximate, such as phenyl optionally substituted by halogen, nitro and/or by lower alkyl, methyl, or benzyl optionally substituted by nitro, or represents a protecting group that can be removed by metal ions, such as 8-quinolyl or 5-chloro-8-quinolyl.

Subsequently, a resulting compound of the formula VIII, in which $R^1$, $X^2$ and $R^2$ have the meanings given above, is first optionally reacted with a 2-substituted ethanol, which converts the radical $X^2$ into a group $OR^3$ in which $R^3$ represents cyanoethyl, 2-trihaloethyl, 2-arylsulphonylethyl, 2-lower alkylthioethyl, 2-arylthioethyl or 2-(4-nitrophenyl)-ethyl, and then the protecting group $R^1$ is removed, and the resulting compound of the formula IX is reacted with another compound of the formula VIII, optionally in the presence of dehydrating agents or in the presence of bases, to form a dinucleotide X (scheme 2). Optionally, a compound of the formula VIII is converted by reaction with bases and water into a different compound of the formula VIII in which $X^2$ represents hydroxy or a salt derived therefrom.

The reactions are carried out in one of the abovementioned inert solvents at room temperature or slightly elevated or reduced temperature, for example at room temperature.

The removal of the protecting group $R^1$ is carried out, for example, by means of acids, such as a mineral

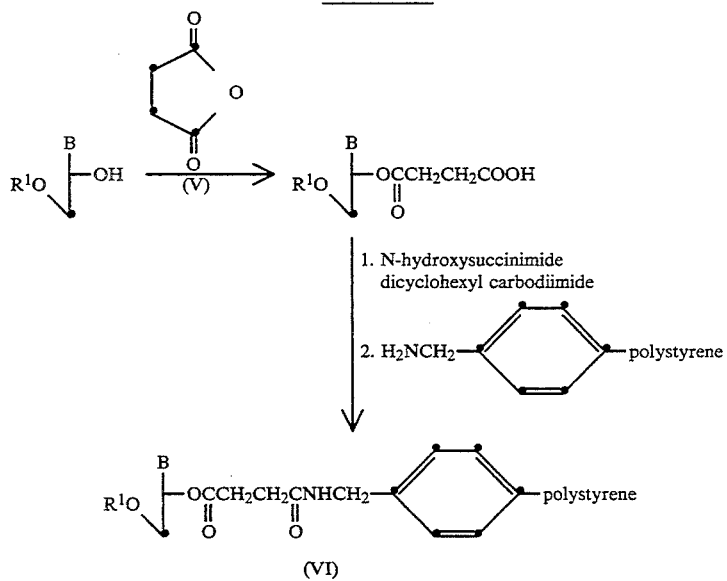

Scheme 1

In the manufacture in accordance with the invention of di-, tri- or tetra-nucleotides according to step b) (scheme 2), nucleosides of the formula V protected in the 5'-position and optionally in the base moiety, in which $R^1$ and B have the meanings given above, are acid, for example hydrochloric acid or sulphuric acid, a carboxylic acid, for example acetic acid, trichloroacetic acid or formic acid, a sulphonic acid, for example methane- or p-toluene-sulphonic acid, or especially a Lewis acid, for example zinc chloride, zinc bromide, aluminium chloride, a dialkylaluminium halide, for example dibutyl- or diethyl-aluminium chloride, or boron trifluoride, at from 10° C. to 50° C., especially at room temperature When using a dialkylaluminium halide, the removal is carried out in a lipophilic solvent, especially in toluene and, when using another of the mentioned Lewis acids, in a solvent mixture consisting of a halogenated hydrocarbon, for example methylene chloride, and a lower alkanol, for example ethanol or isopropanol.

Scheme 2

$$(V) + (VII) \longrightarrow (VIII) \longrightarrow (IX)$$

$$VIII + IX \longrightarrow X$$

The manufacture of dinucleotides of the formula X includes also the reaction of nucleosides of the formula V, in which $R^1$ and B have the meanings given above, with phosphites of the formula VIIA, in which $X^1$ represents halogen, especially chlorine, $X^2$ represents halogen, especially chlorine, or di-lower alkylamino, especially dimethylamino or diisopropylamino, or morpholino, piperidino or pyrrolidino, and $R^2$ has the meaning given above for formula VII, especially methyl, optionally in the presence of a suitable base (scheme 3). The compound of the formula VIIIA obtainable in accordance with the invention either is reacted with a 2-substituted ethanol, which converts the radical $X^2$ into a group $OR^3$ in which $R^3$ has the meanings given above, and is then oxidised with an oxidising agent, for example iodine in the presence of a base, to form the phosphate, and the protecting group $R^1$ is removed, yielding a compound of the formula IX, or is reacted with a compound of the formula IX, then oxidised with an oxidising agent, for example iodine in the presence of a base, to form a compound of the formula X.

Scheme 3

$$(V) + (VIIA) \longrightarrow (VIIIA) \xrightarrow[\text{2. Oxidation}]{\substack{1. R^3OH \\ 3. \text{ Removal of } R^1}} (IX)$$

$$\downarrow \substack{1. IX \\ 2. \text{Oxidation}}$$

$$(X)$$

For the manufacture in accordance with the invention of trinucleotides, the protecting group $R^1$ in dinucleotides of the formula X, in which $R^1$, $R^2$ and $R^3$ have the meanings given above and each of $B^1$ and $B^2$ independently of the other, represents thymyl, cytosyl, adenyl or guanyl, is removed, and the resulting compound is reacted with a compound of the formula VIII, optionally in the presence of dehydrating agents or in the presence of bases, or with a compound of the formula VIIIA followed by oxidation, yielding a compound of the formula XI (scheme 4). The removal of the protecting group $R^1$ and the condensation to form the trinucleotides of the formula XI are carried out in the same manner as described for the manufacture of the dinucleotides of the formula X.

Scheme 4

$$X \longrightarrow \text{(intermediate)} \xrightarrow[\substack{1. VIIIA \\ 2. \text{Oxidation}}]{VIII \text{ or}} (XI)$$

For the manufacture in accordance with the invention of tetranucleotides, trinucleotides of the formula XI are reacted as described above for dinucleotides of the formula X.

In a preferred arrangement of the invention there is used as protecting group $R^1$ a 4-methoxytrityl group, as protecting group $R^2$ a phenyl group substituted by chlorine, especially 2-chlorophenyl, and as protecting group $R^3$ a 2-cyanoethyl group. 1-Benztriazolyloxy is preferred as radical $X^1$ and $X^2$ in the compound of the formula VII.

Trinucleotides of the formula XI are preferably manufactured by removing the protecting group $R^1$ from dinucleotides of the formula X and reacting the resulting compound with a compound of the formula VIII in which $X^2$ represents hydroxy or a salt derived therefrom, in the presence of a dehydrating agent (scheme 4). Dehydrating agents according to the invention are, for example, 2,4,6-trimethylbenzenesulphonyl or triisopropylbenzenesulphonyl chloride, imidazole, tetrazole or 1,2,4-triazole, optionally substituted by nitro. 1-(2,4,6-trimethylbenzenesulphonyl)-3-nitro-1,2,4-triazole (XII) is preferred as dehydrating agent.

The nucleosides used are preferably those in which the free amino group is protected in the base moiety. Preferred protecting groups are benzoyl for adenine, benzoyl or 4-methoxybenzoyl for cytosine, and isobutyryl or diphenylacetyl for guanine. Thymine is preferably used without a protecting group.

In the manufacture according to the invention of oligonucleotides in accordance with step c), an apparatus that is known per se with a semi-automatic or fully automatic, microprocessor-controlled feed system for solvents and reagents is used. In a compound of the formula VI produced according to step a), the protecting group $R^1$ is removed as described above and the resulting compound is then reacted, optionally in the presence of a dehydrating agent or in the presence of a base, either with a compound of the formula VIII, or with a compound of the formula VIIIA, or with a compound of the formula X or XI, in which the protecting group $R^3$ has previously been removed with bases (a 2-cyanoethyl group is removed, for example, with a tri-lower alkylamine, for example triethylamine, in one of the above-mentioned inert solvents or solvent mixtures at from 10° C. to 40° C. especially at room temperature). The invention also includes reactions in which there is used instead of a dinucleotide of the formula X or a trinucleotide of the formula XI a tetranucleotide produced in accordance with step b). If a phosphite of the formula VIIIA is used, subsequent treatment with an oxidising agent, for example iodine in the presence of a base, is carried out. The compound of the formula XIII produced in this manner, in which $R^1$, $R^2$ and B have the meanings given above and n is an integer of from 1 to 4, is subjected to the reaction steps described for the compound of the formula VI (removal of $R^1$, reaction with VIII, VIIIA, X, XI or the corresponding tetranucleotide, optionally with oxidative after-treatment) as often as is necessary to produce a compound of the formula XIII in which n is any integer between approximately 19 and approximately 69.

In a preferred embodiment of the invention, 4-methoxytrityl is used as protecting group $R^1$ and the removal of this group is carried out with zinc bromide in the presence of a CH- or NH-acid compound, especially 1,2,4-triazole or tetrazole. The use of, for example, 1,2,4-triazole for the removal of the 4-methoxytrityl protecting group is novel, and surprisingly results in the removal being quick and producing high yields without side reactions. Especially preferred is the use of zinc bromide and 1,2,4-triazole in a molar ratio of between 20:1 and 100:1 in a solvent mixture consisting of an aprotic solvent and an alcohol, for example methylene chloride and 2-propanol.

In a preferred embodiment of the invention, a compound of the formula VI or of the formula XIII, in which the protecting group $R^1$ has been removed, is reacted with a trinucleotide of the formula XI, in which the protecting group $R^3$ has been removed, in the presence of a dehydrating agent, such as, for example, 2,4,6-trimethylbenzenesulphonyl or triisopropylbenzenesulphonyl chloride, imidazole, tetrazole or 1,2,4-triazole optionally substituted by nitro. Especially preferred is 1-(2,4,6-trimethylbenzenesulphonyl)-3-nitro-1,2,4-triazole (XII).

The especially preferred combination, comprising using as protecting group $R^1$ a 4-methoxytrityl group, using zinc bromide in the presence of 1,2,4-triazole to remove $R^1$ and using a triazole of the formula XII as dehydrating agent for the reaction of oligonucleotidepolystyrene resin of the formula XIII from which the protecting group has been removed with a trinucleotide of the formula XI from which the protecting group has been removed, surprisingly makes it possible for even long nucleotide chains having from approximately 40 to approximately 70 bases to be produced within a short time, in high yields and with high purity.

Processes that are known per se are used for the removal in accordance with the invention of oligodeoxynucleotides from the carrier and for the removal of the protecting groups in accordance with step d). An especially preferred reagent for the removal from the carrier and for the removal of the preferred 2-chlorophenyl protecting group is an aryl aldoximate, for example 1,1,3,3-tetramethylguanidinium 2-nitrobenzaldoximate. The reaction is carried out in one of the above-mentioned inert solvents, to which some water has been added, for example in 95% strength pyridine, at room temperature. Subsequently, reaction with aqueous ammonia at room temperature or elevated temperature, for example at from 20° C. to 70° C., especially at 50° C., is carried out.

For the ligation of the oligodeoxynucelotides according to the invention, a phosphate radical is introduced at the 5'-terminal hydroxy group. The introduction of the phosphate radical (phosphorylation) is carried out in a manner known per se using $T_4$ polynucleotide kinase in the presence of ATP.

Oligodeoxynucelotides produced in accordance with

XIII

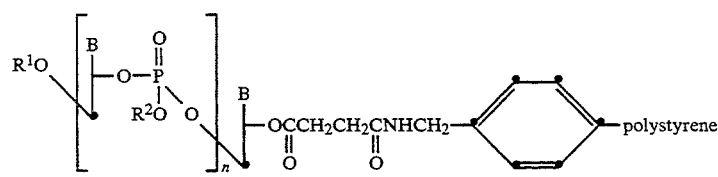

the invention consisting of the coding and the complementary DNA strand contain overlapping sequences consisting of at least 3, and preferably from 8 to 15, overlapping base pairs. Such oligodeoxynucelotide pairs are held together during mixing by hydrogen bonding. The projecting single-stranded ends act in accordance with step e1) and e2) as a matrix (template) for the synthesis of the second (complementary) strand using a DNA polymerase, for example DNA polymerase I, Klenow fragment of DNA polymerase I or $T_4$ DNA polymerase, or using AMV reverse transcriptase, in the presence of the four deoxynucleoside triphosphates (dATP, dCTP, dGTP and TTP). The duplex DNAs formed during complementing, which are especially fragments of the desulphatohirudin gene (process e1) or are the complete desulphatohirudin gene (process e2), have blunt ends.

The fragments of the desulphatohirudin gene obtainable in accordance with process step e1) contain at the ends nucleotide sequences that can be recognised and cleaved by restriction endonucleases. Depending on the choice of nucleotide sequences and accordingly of the restriction endonucleases, during the cleavage completely base-paired (blunt) ends or ends with an overlapping DNA strand (staggered ends) are formed. The restriction recognition sequences are so selected that the ligation of the DNA fragments, which have been treated with a restriction endonuclease forming blunt ends, or the base pairing of the cohesive ends and the subsequent ligation of DNA fragments with projecting DNA strands produces the complete desulphatohirudin structural gene. The ligation of two double-stranded DNA fragments requires a 5'-terminal phosphate group on the donor fragment and a free 3'-terminal hydroxy group on the acceptor fragment. The DNA fragments obtained in step e1) are already 5'-terminally phosphorylated and are linked in a manner known per se using a ligase, especially $T_4$ DNA ligase.

In one embodiment of the present invention, two fragments of the desulphatohirudin gene, especially fragments $F_1$ and $F_2$ according to the formula III and IV respectively, are produced by the method described. The fragments, which if necessary can be subcloned in a suitable vector, contain, preferably at the linking ends, in each case the recognition sequence for a restriction endonuclease, especially EcoRII, which is why after cleavage with the said restriction enzyme and ligation of the two fragments the correctly coding desulphatohirudin DNA sequence is obtained. In addition, fragment 1 before the translation start signal (ATG) and fragment 2 after the translation stop signal (for example TAG) contains additional "terminal" restriction sites which permit the insertion of the desulphatohirudin gene or the desulphatohirudin gene fragments into a suitable vector.

For example, the invention relates to the manufacture of the desulphatohirudin gene in two fragments $F_1$ and $F_2$ of the formula III and IV respectively, which are optionally subcloned and, after cleavage with the restriction enzyme EcoRII and ligation, yield the correct desulphatohirudin DNA sequence, and in which $F_1$ before the translation start signal has an EcoRI restriction site and $F_2$ after the translation stop signal has a BamHI restriction site.

In a preferred embodiment (process e2), each two oligodeoxynucleotides, which alternately originate from the coding and from the complementary strand, are annealed by means of at least 3, and preferably from 8 to 15, complementary bases, are filled up with a DNA polymerase, for example one of those mentioned above, and are ligated using $T_4$ DNA ligase to form the desulphatohirudin structural gene.

Manufacture of expression vectors that contain a gene coding for the amino acid sequence of hirudin The invention relates furthermore to expression vectors that contain a DNA sequence coding for desulphatohirudin, which sequence is regulated by an expression control sequence in such a manner that polypeptides having hirudin activity are expressed in a host cell transformed with these expression vectors.

The expression vectors of the present invention are produced, for example, by inserting a DNA sequence coding for desulphatohirudin into a vector DNA that contains an expression control sequence in such a manner that the expression control sequence regulates the said DNA sequence.

The selection of a suitable vector is determined by the host cell provided for the transformation. Suitable hosts are, for example, microorganisms, such as yeasts, for example *Saccharomyces cerevisiae*, and especially bacterial strains that have no restriction or modification enzyme, especially strains of *Escherichia coli*, for example *E. coli* X1776, *E. coli* HB101, *E. coli* W3110Δ102, *E. coli* HB101/LM1035, *E. coli* JA221 (30) or *E. coli* K12 strain 294, *Bacillus subtilis*, *Bacillus stearothermophilus*, Pseudomonas, Haemophilus, Streptococcus, and others, and also cells of higher organisms, especially established human or animal cell lines. Preferred host cells are the mentioned strains of *E. coli*, especially *E. coli* HB101, *E. coli* JA221 and *E. coli* W3110Δ102.

There are suitable, in principle, all those vectors which replicate and express in the selected host the heterologous DNA sequences according to the invention that code for the amino acid sequence of hirudin.

Examples of vectors that are suitable for the expression of the desulphatohirudin gene in an *E. coli* strain are bacteriophages, for example derivatives of the bacteriophage λ, or plasmids, such as, especially, the plasmid colE1 and its derivatives, for example pMB9, pSF2124, pBR317 or pBR322. The preferred vectors of the present invention are derived from plasmid pBR322. Suitable vectors contain a complete replicon and a marker gene, which renders possible the selection and identification of the microorganisms transformed by the expression plasmids by means of a phenotype feature. Suitable marker genes impart to the microorganism, for example, resistance to heavy metals, antibiotics and the like. Furthermore, preferred vectors of the present invention contain outside the replicon and marker gene regions recognition sequences for restriction endonucleases, so that the DNA sequence coding for the amino acid sequence of hirudin and optionally the expression control sequence can be inserted at these sites. The preferred vector, plasmid pBR322, contains an intact replicon, marker genes ($tet^R$ and $amp^R$) imparting resistance to tetracycline and ampicillin, and a series of recognition sequences, occurring only once, for restriction endonucleases, for example PstI (cleaves in the $amp^R$ gene, the $tet^R$ gene remains intact), BamHI, HindIII, SalI (all cleave in the $tet^R$ gene, the $amp^R$ gene remains intact), NruI and EcoRI.

Several expression control sequences can be used for regulating the desulphatohirudin expression. Especially expression control sequences of strongly expressed genes of the host cell to be transformed are used. When using pBR322 as hybrid vector and *E. coli* as host microorganism, suitable expression control sequences (which inter alia contain the promoter and the ribosomal binding site) are those of the lactose operon, the tryptophan operon, the arabinose operon and the like, and of the β-lactamase gene, the corresponding sequences of the phage λN-gene or of the phage fd-layer protein gene, and others. Whereas the promoter of the β-lactamase gene (β-lac-gene) is already contained in the plasmid pBR322, the other expression control sequences must be introduced into the plasmid. In the present invention, the preferred expression control sequence is that of the tryptophan operon (trp po).

Vectors suitable for replication and expression in yeast contain a yeast-replication origin and a selective genetic marker for yeast. Hybrid vectors that contain a yeast replication origin, for example the chromosomal autonomously replicating segment (ars), are retained extrachromosomally within the yeast cell after transformation and are replicated autonomously during mitosis. Also, hybrid vectors that contain sequences homologous to the yeast 2μ plasmid DNA can be used. Such hybrid vectors are integrated by recombination in 2μ plasmids already present within the cell, or replicate autonomously. 2μ sequences are especially suitable for plasmids having a high transformation frequency and permit a high copy number. Suitable marker genes for yeast are especially those that impart antibiotic resistance to the host or, in the case of auxotrophic yeast routants, genes that complement the host lesions. Corresponding genes impart, for example, resistance to the antibiotic cycloheximide or provide for prototrophy in an auxotrophic yeast mutant, for example the URA3, LEU2, HIS3 or, especially, the TRPI gene. Preferably, yeast hybrid vectors furthermore contain a replication origin and a marker gene for a bacterial host, especially E. coli, so that the construction and the cloning of the hybrid vectors and their precursors can be carried out in one bacterial host. Expression control sequences suitable for expression in yeast are, for example, those of the TRPI, ADHI, ADHII, PHO3 or PHO5 gene, and also promoters involved in glycolysis, for example the PGK and the GAPDH promoter.

The invention relates especially to expression vectors capable of replication and phenotypic selection that contain an expression control sequence and a DNA sequence coding for the amino acid sequence of hirudin, wherein the said DNA sequence together with transcription start signal and termination signal and translation start signal and stop signal in the said expression plasmid is so arranged, with regulation of the said expression control sequence, that desulphatohirudin is expressed in a host cell transformed with the said expression plasmid.

In order to achieve effective expression, the desulphatohirudin gene must be correctly arranged ("in phase") with the expression control sequence. It is advantageous to link the expression control sequence into the region between the main mRNA origin and the ATG of the gene coding sequence, which is naturally linked to the expression control sequence (for example the β-lac coding sequence when using the β-lac promoter), with the desulphatohirudin gene, which preferably has its own translation start signal (ATG) and translation stop signal (for example TAG). An effective transcription and translation is thus ensured.

For example, a vector, especially pBR322, is cleaved with a restriction endonuclease and, optionally after modification of the resulting linearised vector, an expression control sequence provided with corresponding restriction ends is introduced. The expression control sequence contains at the 3'-end (in the translation direction) the recognition sequence of a restriction endonuclease, so that the vector already containing the expression control sequence can be digested with the said restriction enzyme, and the desulphatohirudin gene provided with matching ends can be inserted. The result is a mixture of two hybrid plasmids which contain the gene in the correct and in the incorrect orientation, respectively. It is advantageous to cleave the vector already containing the expression control sequence with a second restriction endonuclease within the vector DNA and to insert into the resulting vector fragment the desulphatohirudin gene provided with correct ends. All operations on the vector are carried out preferably in such a manner that the function of the replicon and of at least one marker gene is not impaired.

In a preferred embodiment of the present invention, a vector derived from pBR322 that contains an expression control sequence, especially that of the tryptophan operon (trp po), which at the 3'-end (between the main mRNA origin and the first ATG) carries the recognition sequence for a restriction endonuclease preferably forming cohesive ends, for example EcoRI, is digested with the mentioned restriction endonuclease and, in the vector DNA fragment, with a second restriction endonuclease that forms blunt, or preferably cohesive, ends, for example BamHI, after which the so linearised vector is linked with the desulphatohirudin gene having corresponding ends (for example with an EcoRI end before the ATG start and a BamHI end after the translation stop codon). The linking is carried out in known manner by pairing the complementary (cohesive) ends and ligation, for example with T4 DNA ligase.

The desulphatohirudin gene, obtained synthetically or from genomic DNA by the mRNA route, and provided with corresponding cohesive (especially EcoRI and BamHI) ends can, before introduction into an expression plasmid, also be cloned into a vector, for example pBR322, in order to obtain larger amounts of the desulphatohirudin gene, for example for the sequence analysis. The isolation of the clones that contain the hybrid plasmid is carried out, for example, with a desulphatohirudin gene-specific, radioactively labelled oligodeoxynucleotide probe (see above). The characterisation of the desulphatohirudin gene is effected, for example, in accordance with the process according to Maxam and Gilbert (11).

In a further embodiment of the invention, two fragments of the desulphatohirudin gene are synthesised. Fragment 1, which includes the first part of the gene, contains before the ATG and at the end in each case the recognition sequence for restriction endonucleases forming cohesive ends, for example before the ATG EcoRI and at the end EcoRII. Fragment 2, which includes the latter part of the gene, has corresponding recognition sequences, for example EcoRII at the beginning, and BamHI after the translation stop signal (for example TAG). The fragments are cleaved at the outer recognition sequences (fragment 1, for example, with EcoRI and fragment 2 correspondingly with BamHI) and subcloned into a correspondingly cleaved vector (for example pBR322). The identification of the clones that contain the fragments and the characterisation of the fragments are effected as described above. The fragments are then cut out of the hybrid vectors with the corresponding restriction endonucleases (fragment 1, for example, with EcoRI and EcoRII and fragment 2, for example, with EcoRII and BamHI) and ligated by way of their cohesive ends, especialy EcoRII ends, resulting in the complete desulphatohirudin gene, which is introduced into a vector ONA in the manner indicated.

Transformation of the microorganisms

The invention relates also to a process for the manufacture of transformed host cells, characterised in that a host cell is transformed with an expression vector that contains a DNA sequence regulated by an expression control sequence and coding for the amino acid sequence of hirudin.

Suitable host cells are, for example, the above-mentioned microorganisms, such as strains of *Saccharomyces cerevisiae*, *Bacillus subtilis* and, especially, *Escherichia coli*. The transformation with the expression plasmids according to the invention is carried out, for example, in the manner described in the literature, for example for *S. cerevisiae* (12), *B. subtilis* (13) and *E. coli* (14). The isolation of the transformed host cells is effected advantageously from a selective nutrient medium to which there has been added the biocide against which the marker gene contained in the expression plasmid imparts resistance. If, as preferred, the expression plasmids contain the amp$^R$ gene, ampicillin is accordingly added to the nutrient medium. Cells that do not contain the expression plasmid are destroyed in such a medium.

The invention relates also to the transformed host cells obtainable in the manner mentioned.

Cultivation of the transformed host cells and the production of desulphatohirudin The transformed host cells can be used for the manufacture of compounds with hirudin activity. The process for the manufacture of these compounds is characterised in that the transformed host cells are cultivated and the product is freed from the host cells and isolated.

There are to be understood by "compounds with hirudin activity" those polypeptides expressed by the mentioned transformed host cells that have a thrombin-inhibiting action and a positive reaction with antihirudin antibodies and that have the primary structure of desulphatohirudin or a structure derived therefrom. There are to be understood by desulphatohirudin compounds having a structure derived from the primary structure of desulphatohirudin modified desulphatohirudin compounds in which the modification resides preferably in a shortening of the primary structure of desulphatohirudin, for example by from 1 to 10, especially from 1 to 6, amino acid building blocks at the N-terminus and/or by from 1 to 6, especially 2, amino acid building blocks at the C-terminus, or in a modification at the N-terminus, for example an N-terminal acetylation or methionylation, of the desulphatohirudin molecule.

The invention therefore relates especially to a process for the manufacture of compounds with hirudin activity and salts of such compounds, characterised in that host cells transformed with an expression plasmid that contains a DNA sequence coding for the amino acid sequence of hirudin and regulated by an expression control sequence are cultivated in a liquid nutrient medium that contains assimilable carbon and nitrogen sources, and the product is freed from the host cells and isolated and, if necessary, there is added to a product obtainable according to the process a reducing agent suitable for cleaving the disulphide bonds, and the resulting reduced polypeptide is treated with an oxidising agent suitable for the new linking of disulphide bonds and, if desired, a resulting hirudin compound is converted into a different hirudin compound and, if desired, a mixture of compounds with hirudin activity obtainable according to the process is separated into the individual components and/or, if desired, a resulting salt is converted into the free polypeptide or a resulting polypeptide is converted into a salt thereof.

The present invention relates especially to a process for the manufacture of hirudin compounds of the formula $$\begin{array}{l}\text{VValTyrThrAspCysThrGluSerGlyGlnAsnLeuCysLeuCysGluGlySerAsnValCys} \\ \text{GlyGlnGlyAsnLysCysIleLeuGlySerAspGlyGluLysAsnGlnCysValThrGlyGluGly} \\ \text{ThrProLysProGlnSerHisAsnAspGlyAspPheGluGluIleProGluGluWLeuGln}\end{array} \quad (\text{XIV})$$

in which V represents Val or Met-Val and W represents Tyr or Tyr(—OSO$_3$H), and salts of such compounds.

The invention relates especially to processes for the manufacture of desulphatohirudin of the formula XIV in which V represents Val and W represents Tyr.

In the compounds with hirudin activity obtainable according to the process, especially in the compounds of the formula XIV, the cysteine residues Cys are preferably linked in pairs by disulphide bridges in the same arrangement as in natural hirudin.

The cultivation of the transformed host cells according to the invention is effected in a manner known per se. For example, various carbon sources can be used for the cultivation of the transformed host microorganisms according to the invention. Examples of preferred carbon sources are assimilable carbohydrates, such as glucose, maltose, mannitol or lactose, or an acetate, which can be used either alone or in suitable mixtures. Suitable nitrogen sources are, for example, amino acids, such as casamino acids, peptides and proteins and their degradation products, such as tryptone, peptone or meat extracts; also yeast extracts, malt extract, and also ammonium salts, for example ammonium chloride, sulphate or nitrate, which can be used either alone or in suitable mixtures. Inorganic salts, which can also be used, are, for example, sulphates, chlorides, phosphates and carbonates of sodium, potassium, magnesium and calcium.

Furthermore, the medium contains, for example, growth-promoting substances, such as trace elements, for example iron, zinc, manganese and the like, and preferably substances that exert a selection pressure and prevent the growth of cells that have lost the expression plasmid. Thus, for example, ampicillin is added to the medium when the expression plasmid contains an amp$^R$ gene. Such an addition of antibiotically active substances also has the effect of destroying the contaminating antibiotic-sensitive microorganisms.

The cultivation is carried out in accordance with processes that are known per se. The cultivating conditions, such as temperature, pH value of the medium and fermentation time, are so selected that maximum hirudin titres are obtained. Thus, an *E. coli* or a yeast strain is preferably cultivated under aerobic conditions in submersed culture with shaking or stirring at a temperature of approximately from 20° to 40° C., preferably approximately 30° C. and a pH value of frown 4 to 9, preferably pH 7, for approximately from 4 to 20 hours, preferably from 8 to 12 hours. During cultivation, the expression product accumulates intracellularly.

When the cell density has reached an adequate value, the cultivation is terminated and the product is freed from the cells of the microorganism. For this purpose the cells are destroyed, for example by treatment with a detergent, such as SDS or Triton, or are lysed with lysozyme or a similarly acting enzyme. Alternatively, or in addition, mechanical forces, such as shearing forces (for example X-press, French press, Dyno-mill)

or shaking with glass beads or aluminium oxide, or alternate freezing, for example in liquid nitrogen, and thawing, for example to from 30° to 40° C., and ultrasound, can be used to break the cells. The resulting mixture, which contains proteins, nucleic acids and other cell constituents, after centrifuging is enriched in a manner known per se with regard to the protein content. Thus, for example, the nonprotein constituents are for the most part removed by polyethyleneimine treatment and the proteins, including the hirudin compounds, are precipitated, for example by saturating the solution with ammonium sulphate or with other salts. Bacterial proteins can also be precipitated by means of acidification with acetic acid (for example 0.1%, pH 4–5). A further enrichment of hirudin compounds can be achieved by extracting the acetic acid supernatant with n-butanol. Other purification steps include, for example, chromatographic processes, such as ion exchange chromatography, gel filtration chromatography, partition chromatography, HPLC, reverse phase HPLC and the like. Thus, the separation of the constituents of the mixture is effected by dialysis, according to charge by means of gel electrophoresis or carrier-free electrophoresis, according to molecular size by means of a suitable Sephadex column, by affinity chromatography, for example with antibodies, especially monoclonal antibodies, or with thrombin coupled to a suitable carrier for affinity chromatography, or by other processes, especially those known from the literature.

For example, the isolation of the expressed hirudin compounds comprises the following steps:

Separation of the cells from the culture solution by centrifugation, production of a crude extract by destroying the cells, for example by treatment with a lysing enzyme and/or alternate freezing and thawing again;

Removal by centrifugation of the insoluble constituents;

Precipitation of the DNA by the addition of polyethyleneimine;

Precipitation of the proteins by ammonium sulphate;

Affinity chromatography of the dissolved precipitate on a monoclonal anti-desulphatohirudin antibody column or a thrombin column;

Desalination of the resulting solution by means of dialysis or chromatography on Sephadex G25 or Sephadex G10.

Alternatively, after separating off the DNA the bacterial proteins can be precipitated by means of 1% acetic acid and the hirudin compound extracted from the acidic supernatant with n-butanol, or the acidic supernatant can be subjected directly to ion exchange chromatography (for example on diethylaminoethylcellulose DEAE 53). Other purification steps include gel filtration on Sephadex G50 (or G75), and reverse phase HPLC. Desalination is effected again on Sephadex G25.

The test with anti-hirudin or anti-desulphatohirudin antibodies (for example monoclonal antibodies obtainable from rabbits or from hybridoma cells), the thrombin test (15) or the blood coagulation test (6) can be used to detect the hirudin activity.

Hirudin compounds obtainable in accordance with the process can be converted in a manner known per se into different hirudin compounds.

Thus, for example, compounds of the formula XIV in which W represents Tyr can be converted by reaction with a tyrosine sulphotransferase, obtainable, for example, from leech cells, into compounds of the formula XIV in which W represents Tyr($-OSO_3H$).

Further, for example, compounds of the formula XIV in which V represents Met-Val can be converted into compounds of the formula XIV in which V represents Val. For example, hirudin compounds having an N-terminal methionyl residue obtainable in accordance with the invention can be converted into corresponding compounds without an N-terminal methionyl residue by removing the terminal methionyl residue in customary manner by means of cyanogen bromide. The reaction with cyanogen bromide is carried out, for example, in an aqueous acidic medium, for example in strongly diluted hydrochloric acid, for example in 0.1–0.3N hydrochloric acid, or in a strong organic acid, for example in 50–70% formic acid, at room temperature or slightly elevated or reduced temperature, for example at from approximately 15° to approximately 25° C., over a period of approximately 24 hours.

Earlier tests have shown that the unimpaired state of the disulphide bridges is of importance for the coagulation-inhibiting activity of natural hirudin (cf. Lit. ref. 2). Depending on the choice of host cell, linking of the six cysteine radicals in the primary translation product, to form the three disulphide bridges, in a manner different from the natural process occurring in leech cells cannot be excluded. It is possible that the resulting "false" tertiary structure of the product results in a reduction or even the loss of the valuable pharmacological properties, especially the coagulation-inhibiting activity, which can be ascertained by means of the above-mentioned hirudin assay (for example thrombin test). In such a case it is expedient to cleave the disulphide bonds with a suitable reducing agent and to treat the reduced polypeptide with a suitable oxidising agent for the new linking of disulphide bonds. On the basis of the hirudin activity of the formed product (for example in the thrombin test), it is possible to ascertain whether the chosen conditions (reducing and/or oxidising agent) have led to the desired biologically active hirudin or whether the conditions must be modified in known manner.

Suitable reducing agents for cleaving disulphide bonds are, for example, thiol compounds, such as thiophenol, 4-nitrothiophenol, 1,4-butanedithiol and, especially, 1,4-dithiothreitol. The reduction is advantageously carried out in an aqueous alkaline medium, for example in the dilute aqueous solution of an alkali metal hydroxide, for example sodium hydroxide, of an alkali metal carbonate, for example sodium carbonate, or of an organic base, especially a tri-lower alkylamine, for example triethylamine, at room temperature.

Oxidising agents suitable for the new linking of disulphide bonds in the reduced polypeptides are, for example, atmospheric oxygen, which is conveyed through an aqueous solution of the polypeptide to which there has optionally been added a catalytic amount of a transition metal salt, for example iron(III) sulphate, iron(III) chloride or copper(II) sulphate; iodine, also in the form of the potassium iodide adduct $KI_3$, which is preferably used in alcoholic, for example methanolic, or aqueous alcoholic, for example aqueous methanolic, solution; potassium hexacyanoferrate (III) in aqueous solution; and 1,2-diiodoethane or azodicarboxylic acid dimethyl ester or diethyl ester, which can be reacted in water or in a mixture consisting of water and a water-miscible alcohol, for example methanol. The oxidation is carried out especially at room temperature.

The removal of the reagents, especially the salts and the oxidising and reducing agents and their secondary products, from the desired hirudin compound is effected in accordance with methods that are known per se, for example by molecular weight filtration, for example over Sephadex or Biogel.

A mixture of compounds with hirudin activity obtainable in accordance with the process can be separated into the individual components in a manner known per se. Suitable separating processes are, for example, chromatographic processes, for example adsorption chromatography, ion exchange chromatography, HPLC or reverse-phase HPLC, also multiplicative partitioning or electrophoretic methods, for example electrophoresis on cellulose acetate or gel electrophoresis, especially polyacrylamide gel electrophoresis ("PAGE").

The invention relates furthermore to the novel desulphatohirudin compounds obtainable in accordance with the invention, especially those of the formula XIV in which V represents Met-Val and W has the meanings given, and to salts thereof.

The invention relates further to novel desulphatohirudin compounds which are characterised by RP-HPLC constants [conditions: Vydac 218TP5415; 4.6×150 mm; flow rate 1.2 ml/min.; eluant: A: 0.1% trifluoroacetic acid, B: acetonitrile/water 8:2+0.07% trifluoroacetic acid. Gradient: 2 min. 16% B, then increase in the course of 3 min. to 20% B, then increase in the course of 15 min. to 25% B, then increase in the course of 27 min. to 64% B], FPLC constants [conditions: Mono Q-column (Pharmacia), 4.6 mm×150 min. Buffer A: 20 mM tris.HCl pH 7.5; buffer B: 20 mM tris.HCl/1M NaCl. Linear salt gradient: A: elute in the course of 9 ml with 15% buffer B, increase in the course of 10.7 ml to 70% buffer B] and UV absorption as follows:

Compound A: RP-HPLC, retention time 16.83 min.; FPLC: elution at 390 mM NaCl; UV (water): $\lambda_{max}=275$ nm;

Compound B: RP-HPLC: retention time 18.43 min.;

Compound C: RP-HPLC: retention time 19.6 min.; FPLC: elution at 420 mM NaCl;

Compound D: RP-HPLC: retention time 20.6 min.; FPLC: elution at 460 mM NaCl;

Compound E: RP-HPLC: retention time 21.53 min.; FPLC: elution at 500 mM NaCl; UV (water): $\lambda_{max}=273$ nm;

and the process for the manufacture thereof by means of the transformed host strains.

The compounds that can be produced in accordance with the invention and the novel compounds, for example of the formula XIV, may be not only in free form but also in the form of their salts, especially their pharmaceutically acceptable salts. Since they contain several amino acid residues with free amino groups the compounds according to the invention can, for example, be in the form of acid addition salts. There come into consideration as acid addition salts especially physiologically tolerable salts with customary therapeutically acceptable acids; there may be mentioned as inorganic acids hydrohalic acids, such as hydrochloric acid, and also sulphuric acid and phosphoric or pyrophosphoric acid; suitable organic acids are especially sulphonic acids, such as benzene-or p-toluene-sulphonic acid or lower alkanesulphonic acids, such as methanesulphonic acid, and also carboxylic acids, such as acetic acid, lactic acid, palmitic and stearic acids, malic acid, tartaric acid, ascorbic acid and citric acid. Since the hirudin compounds also contain amino acid residues with free carboxyl groups they can also be in the form of metal salts, especially alkali metal or alkaline earth metal salts, for example sodium, potassium, calcium or magnesium salts, or in the form of ammonium salts derived from ammonia or a physiologically tolerable organic nitrogen-containing base. Since, however, they may contain free carboxyl groups and free amino groups simultaneously, they can also be in the form of internal salts.

Depending on the procedure, the compounds according to the invention are obtained in free form, in the form of acid addition salts or salts with bases. The free compounds can be obtained from the acid addition salts and the salts with bases in a manner known per se, for example by adjusting the pH value to the isoelectric point. From the free compounds it is possible in turn to obtain therapeutically acceptable acid addition salts or salts with bases by reaction with acids or bases, respectively, for example with those that form the above-mentioned salts, and concentration by evaporation or lyophilisation.

Monoclonal antibodies to desulphatohirudin and test kits that contain such antibodies The ability of antibodies to bind specific antigens finds practical use outside the body in the qualitative and quantitative determination of antigens (immunoassay) and in the purification of antigens (immunoaffinity chromatography). Serum of immunised animals normally contains a plurality of different antibodies that react with the same antigen at different binding sites with different affinity, but in addition there are also antibodies to other antigens which reflect the earlier experiences of the individual. The successful use of antibodies for the determination and purification of antigens, however, requires high specificity and reproducibility.

Homogeneous antibodies that meet these requirements have been made available by the hybridoma technique described by Kohler and Milstein (17). In principle, the technique comprises fusing antibody-secreting B-lymphocytes, for example from the spleen, of immunised animals, with tumour cells. The resulting hybridoma cells combine the ability to multiply on an unlimited scale by division with the ability to form and secrete a uniform type of antibody. By cultivating in a selective medium in which non-fused tumour cells die off, but hybridoma cells multiply, and by means of suitable manipulations, clones, that is to say cell populations that are derived from a single hybridoma cell and are genetically identical, can be obtained and cultivated, and the monoclonal antibodies produced by the cells can be isolated.

The present invention relates to monoclonal antibodies to desulphatohirudin and hirudin, hybridoma cells that produce such antibodies and processes for their manufacture. Preferred are hybridoma cell lines and the monoclonal antibodies secreted therefrom that react specifically with desulphatohirudin or hirudin. The process for the manufacture of monoclonal anti-desulphatohirudin and anti-hirudin antibodies is characterised in that mice are immunised with desulphatohirudin or hirudin, B-lymphocytes of animals immunised in such a manner are fused with myeloma cells, the resulting hybridoma cells are cloned, then cultivated in vitro or by injection into mice, and antibodies are isolated from the cultures.

The invention relates further to immunoaffinity chromatography columns and test kits for immunoassays that contain these antibodies.

In accordance with the process of the invention, mice, for example Balb/c mice, are immunised in a manner known per se. Surprisingly the immunisation is successful although desulphatohirudin and hirudin are relatively small protein molecules. In a preferred embodiment in each case desulphatohirudin or hirudin is injected approximately weekly or also at longer intervals for several weeks, for example for 5 to 12 weeks, until an adequate number of antibody-producing B-lymphocytes has formed.

B-lymphocyte-containing organs, for example spleen cells, of the immunised mice are removed and fused with myeloma cells that owing to a mutation do not grow in a selective culture medium. Such myeloma cells are known and are, for example, those designated X63-Ag8, X63-Ag8.6.5.3, MPC-11, NS1-Ag4/1, MOPC-21 NS/1 or SP 2/0. In a preferred embodiment, spleen cells of immunised mice are fused with myeloma cells of the cell line X63-Ag8.5.6.3.

The fusion is carried out according to processes known per se by mixing the B-lymphocytes and myeloma cells with the addition of a cell fusion agent, such as polyethylene glycol, Sendai virus, calcium chloride or lysolecithin. Preferably, fusion is carried out in the presence of polyethylene glycol, for example having a molecular weight of from 1000 to 4000. After the fusion, the resulting hybrids are cultivated in accordance with a process known per se in a selective culture medium that is complemented with hypoxanthine, aminopterin and thymidine (HAT medium). Non-fused myeloma cells cannot grow in this medium and die just like normal lymphocytes.

The supernatants of the hybridoma cultures can be tested by processes known per se for their content of specific antibodies, for example by radio immunoassay or agglutination. In such tests it is surprisingly ascertained that it is possible to obtain with the process described hybridoma cells that secrete antibodies specific to desulphatohirudin or hirudin.

The hybridoma cells that produce antibodies of the desired specificity are selected by means of cloning from the mixture of various hybridoma cells produced from the fusion. For this purpose, in accordance with a process that is known per se, which is called "limiting dilution", cultures are prepared starting from a single growing cell.

For mass production, the hybridoma cell clones that produce antibodies of the desired specificity are either cultivated in vitro in media known per se or injected into mice for multiplication. In a preferred embodiment, hybridoma cells are injected into mice pretreated with pristane, ascites fluid is removed and from this antibodies are isolated by precipitation with ammonium sulphate solution.

The desulphatohirudin- and hirudin-specific antibodies obtained by means of these hybridoma cells can be used in a manner known per se for the manufacture of immunoaffinity chromatography columns. In a preferred embodiment of the invention an antibody solution is added to a suitable carrier (suspended in a buffer solution), unbound portions are then washed out and unoccupied sites on the carrier are blocked.

The desulphatohirudin- and hirudin-specific antibodies obtained by means of the hybridoma cells can be used in a manner known per se for the manufacture of test kits. These test kits can be based on various methods, for example radio-immunodiffusion, latex agglutination, spot tests, competitive or sandwich radioimmunoassay, enzyme immunoassay, immunofluorescence or immunochemical enzyme tests. Such kits may contain apart from customary antibodies of various origins antibody conjugates with enzymes or fluorescence carriers, in addition desulphatohirudin or hirudin labelled with radioactive isotopes such as $I^{125}$, or conjugated with enzymes, for example with horseradish peroxidase or alkaline phosphatase, also enzyme substrates, suitable buffers, gels, latex, polystyrene or other fillers and carriers.

Pharmaceutical preparations

The known ("natural" hirudin) and novel (for example desulphatohirudin) hirudins obtainable in accordance with the present invention have valuable pharmacological properties and can, like hirudin extracted from leeches, be used prophylactically or, especially, therapeutically.

The desulphatohirudin compounds that can be manufactured in accordance with the invention are at least equivalent to natural hirudin as regards their biological activity. Thus, for example, desulphatohirudin has a $K_i$ value of approximately $10^{-11}M$. Desulphatohirudin is completely specific to thrombin and exhibits no interactions with other proteinases of the blood coagulation system. The active toxicity is extremely low; for example, in rats, at a dose of, for example, 1 g/kg, no toxic effects can be detected. Similarly, no hypersensitivity reactions or allergic reactions are observed.

The novel desulphatohirudin compounds according to the invention can therefore be used analogously to natural hirudin for the therapy and prophylaxis of thromboses and thromboembolisms, including the prophylaxis of post-operative thromboses, for acute shock therapy (for example for septic or polytraumatic shock), for the therapy of consumption coagulopathies, in haemodialyses, haemoseparations and in extracorporeal blood circulation.

The invention relates also to pharmaceutical compositions that contain at least one of the compounds according to the invention or pharmaceutically acceptable salts thereof, optionally together with a pharmaceutically acceptable carrier and/or adjuncts.

These compositions can be used especially in the above-mentioned indications, when they are administered, for example, parenterally, such as intravenously, intracutaneously, subcutaneously or intramuscularly, or topically.

The invention relates also to the use of the novel compounds according to the invention and to pharmaceutical compositions containing them for the prophylactic and therapeutic treatment of the human or animal body, especially for the above-mentioned clinical syndromes, especially for inhibiting the coagulation of blood inside and outside the human or animal body.

The dosage depends especially on the specific form of administration and on the purpose of the therapy or prophylaxis. The size of the individual doses and the administration regime can best be determined by way of an individual judgement of the particular case of illness; the methods of determining relevant blood factors required for this purpose are familiar to the person skilled in the art. Normally, in the case of an injection the therapeutically effective amount of the compounds according to the invention is in a dosage range of from approximately 0.005 to approximately 0.1 mg/kg body weight. A range of from approximately 0.01 to approximately 0.05 mg/kg body weight is preferred. The administration is effected by intravenous, intramuscular or subcutaneous injection. Accordingly, pharmaceutical preparations for parenteral administration in single dose form contain per dose, depending on the mode of administration, from approximately 0.4 to approximately 7.5 mg of the compound according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. They may be in freeze-dried or dissolved form, it being possible for solutions advantageously to contain an antibacterially active preservative, for example from 0.2 to 0.3% 4-hydroxybenzoic acid methyl ester or ethyl ester.

A preparation for topical application can be in the form of an aqueous solution, lotion or gel, an oily solution or suspension or a fat-containing or, especially, emulsified ointment. A preparation in the form of an aqueous solution is obtained, for example, by dissolving the active ingredients according to the invention, or a therapeutically acceptable salt thereof, in an aqueous buffer solution of from pH 4 to pH 6.5 and, if desired, adding a further active ingredient, for example an anti-inflammatory agent, and/or a polymeric binder, for example polyvinylpyrrolidone, and/or a preservative. The concentration of active ingredient is from approximately 0.1 to approximately 1.5 mg, preferably from 0.25 to 1.0 mg, in 10 ml of a solution or 10 g of a gel.

An oily form of administration for topical application is obtained, for example, by suspending the active ingredients according to the invention, or a therapeutically acceptable salt thereof, in an oil, optionally with the addition of swelling agents, such as aluminium stearate, and/or surfactants (tensides) having an HLB value ("hydrophilic-lipophilic balance") of below 10, such as fatty acid monoesters of polyhydric alcohols, for example glycerine monostearate, sorbitan monolaurate, sorbitan monostearate or sorbitan monooleate. A fat-containing ointment is obtained, for example, by suspending active ingredients according to the invention, or salts thereof, in a spreadable fatty base, optionally with the addition of a tenside having an HLB value of below 10. An emulsified ointment is obtained by triturating an aqueous solution of the active ingredients according to the invention, or salts thereof, in a soft, spreadable fatty base with the addition of a tenside having an HLB value of below 10. All these forms for topical application can also contain preservatives. The concentration of active ingredient is from approximately 0.1 to approximately 1.5 mg, preferably from 0.25 to 1.0 mg, in approximately 10 g of base.

In addition to the compositions described above and pharmaceutical compositions analogous thereto that are intended for direct medicinal use in the body of a human or a mammal, the present invention relates also to pharmaceutical compositions and preparations for medicinal use outside the living body of humans or mammals. Such compositions and preparations are used especially as anticoagulant additives to blood that is being subjected to circulation or treatment outside the body (for example extracorporeal circulation or dialysis in artificial kidneys), preservation or modification (for example haemoseparation). Such preparations, such as stock solutions or alternatively preparations in single dose form, are similar in composition to the injection preparations described above; however, the amount or concentration of active ingredient is advantageously based on the volume of blood to be treated or, more precisely, on its thrombin content. In this connection it must be borne in mind that the active ingredients according to the invention (in free form) completely deactivate approximately 5 times the amount by weight of thrombin, are physiologically harmless even in relatively large amounts, and are eliminated from the circulating blood very rapidly even in high concentrations so that there is no risk of overdose, even, for example, during transfusions. Depending on the specific purpose, the suitable dose is from approximately 0.01 to approximately 1.0 mg of the active ingredient/liter of blood, although the upper limit may still be exceeded without risk.

The invention relates especially to the DNA sequences coding for the amino acid sequence of hirudin that are described in the Examples, expression plasmids containing such DNA sequences, microorganisms transformed with such expression plasmids, monoclonal antibodies to hirudin, hybridoma cells that produce such antibodies, and test kits for immunoassays that contain such antibodies, the processes for their manufacture described in the Examples and the process described in the Examples for the manufacture of polypeptides with hirudin activity using transformed microorganisms, and to the novel desulphatohirudin compounds described in the Examples.

The following Examples and drawings serve to illustrate the invention and are in no way intended to limit it.

Experimental Section

The meanings of the abbreviations used in the Examples are as follows:
TNE solution that contains 100 mM NaCl, 50 mM tris·HCl pH 7.5 and 5 mM EDTA,
SDS sodium dodecyl sulphate
EDTA ethylenediaminetetraacetic acid
DTT 1,4-dithiothreitol (1,4-dimercapto-2,3-butanediol)
BSA bovine serum albumin
EtBr ethidium bromide
tris tris-(hydroxymethyl)-aminomethane
tris.HCl tris monohydrochloride

EXAMPLE 1

Manufacture of protected nucleoside-polystyrene resin

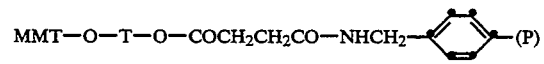

750 mg of succinic acid anhydride and 910 mg of 4-dimethylaminopyridine are added to 2.57 g (5 mmol) of 5'-(4-methoxytrityl)-thymidine (MMT-O-T-OH) in 20 ml of absolute pyridine and the whole is left at room temperature for 16 hours. After concentrating the pyridine solution, this is taken up in 200 ml of ethyl acetate, extracted by shaking twice, with 200 ml of 0.1M phosphate buffer each time with the addition of 10 ml of saturated sodium chloride solution, washed again with saturated sodium chloride solution, dried, concentrated add hexane is added dropwise. The precipitated product is separated off and triturated twice with ether, then dissolved in 300 ml of ethyl acetate and extracted by shaking at 0° C. with 180 ml of 0.1M potassium bisulphate of pH 2.5. After washing twice with water, the ethyl acetate solution is dried with sodium sulphate, filtered, 0.5 ml of pyridine is added and the whole is concentrated and diluted by the dropwise addition of hexane. The precipitated succinic acid derivative is removed by filtration.

1.0 g of this compound are dissolved together with 190 mg of N-hydroxysuccinimide in 4 ml of ethyl acetate and 2 ml of dimethylformamide, and 370 mg of N,N'-dicyclohexylcarbodiimide are added at 0° C. After standing overnight in a refrigerator, the precipitated N,N'-dicyclohexyl urea is filtered off, the filtrate is diluted with ethyl acetate, extracted with cold 0.1M sodium bicarbonate and water, dried and concentrated to dryness by evaporation in vacuo. The residue is chromatographed with ethyl acetate on silica gel. TLC: $R_f$ 0.45 in dichloromethane/methanol (9:1).

100 mg of this N-succinimidoylsuccinic acid ester are stirred for 20 hours with 1 g of aminomethylpolystyrene (amine content 110 μmol/g) in 2 ml of dichloromethane and 4 ml of dimethylformamide. The polymer resin is filtered off and extracted by washing with dimethylformamide, methanol, dichloromethane and methanol. After drying, the amino groups that have not reacted are acetylated by stirring the resin in 6 ml of pyridine with 1 ml of acetic anhydride and 100 mg of 4-dimethylaminopyridine for 30 minutes. The polymer resin is extracted by washing with dichloromethane, dimethylformamide, methanol and dichloromethane, and dried until a constant weight is reached. The spectroscopic methoxytrityl (MMT)-determination gives a charge of 57 μmol/g.

EXAMPLE 2

The following protected nucleoside/polystyrene resin is manufactured analogously to Example 1:

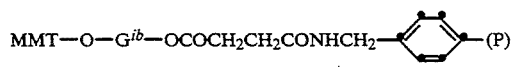

from 5'-(4-methoxy-trityl)-N-isobutyryl-deoxyguanosine, charge 32 μmol/g.

EXAMPLE 3

Synthesis of the trinucleotide

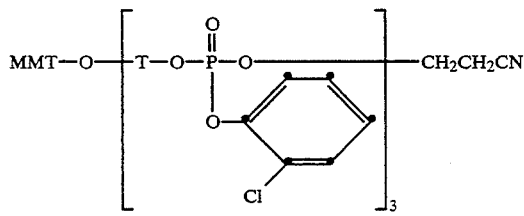

a) Synthesis of the dinucleotide 7.73 g (15 mmol) of 5'-(4-methoxytrityl)-thymidine (MMT-O-T-OH) are twice concentrated by evaporation with absolute pyridine. The residue is dissolved in 20 ml of absolute tetrahydrofuran and added dropwise to 80 ml of a 0.2M solution of 2-chlorophenyl-di-(1-benzotriazolyl)-phosphate in tetrahydrofuran while stirring and with the exclusion of moisture and the reaction mixture is stirred for 1 hour at room temperature. The resulting solution of 2-chlorophenyl-1-benzotriazolyl-5'-(4-methoxytrityl)-thymidine-3'-phosphate is divided into 3 portions.

α) Hydrolysis to triethylammonium-2-chlorophenyl-5'-(4-methoxytrityl)-thymidine-3'-phosphate:

100 ml of 0.5M triethylammonium bicarbonate are added to a third of the above solution of 2-chlorophenyl-1-benzotriazolyl-5'-(4-methoxytrityl)-thymidine-3'-phosphate while cooling. After 15 minutes extraction is carried out with dichloromethane. The dichloromethane solution is washed with water, concentrated, and petroleum ether is added dropwise thereto. The resulting precipitate is filtered off with suction, extracted by washing with ether/petroleum ether 1:1 and dried in vacuo. TLC: $R_f$ 0.35 in dichloromethane/methanol/water (75:22:3).

β) Esterification to 2-cyanoethyl-2-chlorophenyl-5'-(4-methoxytrityl)-thymidine-3'-phosphate and removal of the 4-methoxytrityl protecting group:

1.3 ml of 2-cyanoethanol and 2 ml of pyridine are added to a third of the solution of 2-chlorophenyl-1-benzotriazolyl-5'-(4-methoxytrityl)-thymidine-3'-phosphate. The mixture is left to stand overnight at room temperature. The solvents are distilled off in vacuo and the residue is dissolved in ethyl acetate and repeatedly extracted by shaking with 0.1M phosphate buffer of pH 7 and water. The organic phase is dried, concentrated and added dropwise to hexane. The precipitate is filtered off, dissolved in 50 ml of dichloromethane/methanol 7:3 and, at 0° C., a solution of 3.8 g of p-toluene-sulphonic acid monohydrate in 75 ml of dichloromethane/methanol 7:3 is added. After 2 hours, the reaction solution is diluted with dichloromethane and extracted by shaking with a cold sodium bicarbonate solution. The organic phase is concentrated and hexane is added. The precipitated 2-cyanoethyl-2-chlorophenyl-thymidine-3'-phosphate is chromatographed on silica gel with dichloromethane/methanol 96:4. TLC: $R_f$ of 0.45 in dichloromethane/methanol (9:1).

γ) Condensation to the 5'-(4-methoxytrityl) -3'-cyanoethyl-bis-thymidine dinucleotide:

2.2 g of 2-cyanoethyl-2-chlorophenyl-thymidine-3'-phosphate are dehydrated by twice concentrating by evaporation with absolute pyridine, and the product is dissolved in 20 ml of absolute tetrahydrofuran and added to the remaining third of the solution of 2-chlorophenyl-1-benzotriazolyl-5'-(4-methoxytrityl)-thymidine-3'-phosphate. After 18 hours at room temperature 10 ml of water and 200 ml of ethyl acetate are added to the reaction solution while cooling with ice. The organic phase is washed repeatedly with sodium bicarbonate and water, dried over sodium sulphate and concentrated to a small volume. The dinucleotide, protected in the phosphate moiety and at the 5'- and 3'-end, is precipitated by adding dropwise to ether/hexane 1:1. TLC: $R_f$ 0.48 in dichloromethane/methanol (9:1).

b) Synthesis of the trinucleotide:

1.17 g (1 mmol) of the above-described fully protected dinucelotide are dissolved in 30 ml of dichloromethane/methanol 7:3 and, while cooling with ice, a solution of 1.9 g of p-toluenesulphonic acid monohydrate in 20 ml of dichloromethane/methanol 7:3 is added. After 2 hours, ice-cold sodium bicarbonate solution is added and extraction is carried out with dichloromethane. The organic phase is dried, concentrated and added dropwise to hexane. The precipitated crude dinucleotide with a free 5'-hydroxy group is chromatographed on silica gel with a gradient of 2–8% methanol in dichloromethane. TLC: R_f 0.33 in dichloromethane/methanol (9:1).

850 mg of this 5'-hydroxy-dinucelotide and 1.06 g of triethylammonium-2-chlorophenyl-5'-(4-methoxytrityl)-thymidine-3'-phosphate [cf. paragraph a)α)] are twice concentrated by evaporation with pyridine, then dissolved in 10 ml of absolute pyridine and 560 mg of 1-mesitylenesulphonyl-3-nitro-1,2,4-triazole (MSNT) are added. After 2 hours, 2 ml of ice-cold water are added and, after a further hour, extraction is carried out with dichloromethane. The organic phase is washed with saturated sodium bicarbonate solution and water, dried, concentrated and ether is added. The precipitated trinucleotide is purified by chromatography on silica gel. R_f 0.45 in dichloromethane/methanol (9:1).

EXAMPLE 4

Analogously to Example 3, the following protected trinucleotides of the general formula

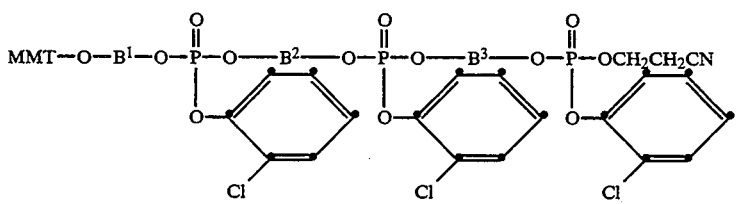

abbreviated to $B^1B^2B^3$, are manufactured. The following abbreviations are used for the nucleosides $B^1$, $B^2$, $B^3$:
A = N-benzoyl-deoxyadenosine
C = N-benzoyl-deoxycytidine
G = N-isobutyryl-deoxyguanosine
T = thymidine

| Compound | R_f[a] | Compound | R_f[a] |
|---|---|---|---|
| TTT | 0.45 | ATG | 0.48 |
| TTC | 0.55 | ACT | 0.53 |
| TCT | 0.46 | ACC | 0.48 |
| TAC | 0.56 | ATT | 0.55 |
| TGC | 0.44 | ACA | 0.53 |
| TAG | 0.60 | AAC | 0.46 |
| TGT | 0.42 | AAA | 0.51 |
| TGA | 0.44 | AGT | 0.45 |
| CTT | 0.53 | AGG | 0.38 |
| CTG | 0.46 | GTT | 0.45 |
| CCT | 0.45 | GTC | 0.44 |
| CCC | 0.59 | GTG | 0.35 |
| CCG | 0.47 | GCA | 0.49 |
| CCA | 0.51 | GCG | 0.48 |
| CAT | 0.55 | GAT | 0.44 |
| CAC | 0.51 | GAC | 0.48 |
| CGC | 0.46 | GAG | 0.48 |
| CGA | 0.38 | GAA | 0.50 |
| CAG | 0.44 | GGC | 0.42 |
| CGG | 0.38 | GGT | 0.46 |
| CGT | 0.49 | GGG | 0.35 |
|  |  | GGA | 0.44 |

[a]Thin layer chromatogram on silica gel in dichloromethane/methanol 9:1

EXAMPLE 5

Synthesis of the DNA fragment of a length of 67 bases from base No. 96 to base No. 162 of the DNA strand 96/97)

a) Removal of the 2-cyanoethyl protecting group from the trinucleotides

10 μmol of the trinucleotides from Example 3 or 4 are dissolved, with the exclusion of moisture, in 60 μl of pyridine/acetonitrile/triethylamine 1:1:1. After 1 hour at room temperature, 0.7 ml of peroxide-free ether is added dropwise and the precipitate is removed by centrifuging. The crude triethylammonium salt is dissolved in 50 μl of pyridine and again precipitated with 0.5 ml of ether, centrifuged off, and dried in a high vacuum for 15 hours.

b) Coupling the partially protected trinucleotides with the oligonucleotide chain bonded to polystyrene resin All operations are carried out with the exclusion of moisture in a reaction vessel of 220 μl capacity with microprocessor-controlled addition of solvent and reagent. 13 mg (0.74 μmol) of the thymidine/polystyrene resin (Example 1) are placed in the reaction vessel and subjected to the following operations:
1. Methylene chloride, 2 ml/min., 4 min.
2. Methylene chloride/isopropanol (85:15), 2 ml/min., 2 min.
3. Zinc bromide 1M and 1,2,4-triazole 0.02M methylene chloride/isopropanol (85:15) , 2 ml/min., 2–3.5 min.
4. Methylene chloride/isopropanol (85:15) , 2 ml/min., 4 min.
5. Triethylammonium acetate 0.5M in DMF, 2 ml/min., 5 min.
6. Molecular sieve-dried pyridine, 2 ml/min., 3 min.
7. Tetrahydrofuran (peroxide-free, molecular sieve-dried), 2 ml/min., 3 min.
8. Nitrogen stream, 10 min.
9. Injection of 10 μmol of trinucleotide GTC (trimethylammonium salt from paragraph a)) and 8.9 mg (30 μmol) of 1-mesitylenesulphonyl-3-nitro-1,2,4-triazole (MSNT) dissolved in 150 μl of pyridine.
10. 45° C., 20 rain.
11. Pyridine, 2 ml/min., 4 min.
12. Acetic anhydride 5% and 4-dimethylaminopyridine 2.5% in pyridine, 2 ml/min., 4 min.
13. Pyridine, 2 ml/min., 4 min.
14. Pyridine/isopropanol (1:1), 2 ml/min., 3 min.

All 14 operations are repeated 21 times, but in the 9th operation, instead of GTC the following trinucleotides, respectively, are used in the form of their triethylammonium salts (paragraph a)) in the sequence indicated: GCA, ACC, GAA, CCC, TAC, AGG, TGA, CGC, TAC, CGT, GTG, CCA, AAA, AAA, TGA, CGG, TGA, TTC, GGG, CCT, CAT. The mean coupling yield is 97%. The end product has the following structure:

MMT-CATCCTGGGTTCTGACGGTGAAAAAAACCAGTGCGTTACCGGTGAAGGTACCCCGAAACCGCAG
TCT-polystyrene c) Removal of the DNA fragment from the carrier and removal of the protecting groups 40.0 mg (approximately 0.60 μmol) of DNA synthesis resin 96/67 are maintained at 50° C. for 3 hours and at room temperature for 12 hours with 66 mg (0.40 mmol) of o-nitrobenzaldoxime and 50 μl (0.40 mmol) of 1,1,3,3-tetramethylguanidine in 400 μl of 95% pyridine. After blowing off the pyridine with nitrogen, 1.6 ml of aqueous ammonia (33%) are added to the residue and the whole is maintained for 24 hours at 50° C. in a closed vessel.

The liquid phase separated off is freed of ammonia in vacuo and washed 3 times with 3 ml of peroxide-free diethyl ether each time. After removing the lower molecular constituents on a Biogel P6 column (100–200 mesh, 3×66 cm, 0.01 molar trimethylammonium bicarbonate pH 7.5, 1.5 ml/min.), 285 ODs (260 nm) of DNA are isolated.

A total of 60 ODs are separated on an HPLC column (PRP-1/Hamilton, 250×4.6 mm). Gradient (solution A: 0.05M triethylammonium acetate pH 7.0; solution B: solution A:acetonitrile 1:1): 30% B in A 60% B in A in 20 min. at 50° C. and 2 ml/min. The lipophilic main peak (retention time approximately 14 min.) is collected, concentrated over a DE52 cellulose (Whatman) column, eluted and precipitatd with ethanol. To remove the 4-methoxytrityl protecting group, the precipitate is dissolved in 50 μl of acetic acid/H₂O (4:1) and maintained at room temperature for 45 minutes. The reaction product is lyophilised, precipitated with ethanol and, for purification, electrophoretically separated on an 8% polyacrylamide gel (7M urea). The band corresponding to the desired DNA size is cut out and the product is electroeluted, concentrated over DE52 cellulose and is precipitated with ethanol.

EXAMPLE 6

The following DNA fragments (5'-3') are produced analogously to Example 5:

1/58
CTGGAATTCATGGTTGTTTACACCGACTGCACCGAATCTGGTCAGAACCTGTGCCTGT

46/64 complementary
CAGAACCCAGGATGCATTTGTTACCCTGACCGCAAACGTTAGAACCTTCGCACAGGCACAGGTT 154/64 complementary
CAGGATCCTACTGCAGGTATTCTTCCGGGATTTCTTCGAAGTCACCGTCGTTGTGAGACTGCGG

EXAMPLE 7

Phosphorylation of the fragments 1/58, 46/64 complementary, 96/67 and 154/65 complementary The phosphorylation and the radioactive labelling at the 5'-ends is effected with [γ-³²P]ATP and T₄ polynucleotide kinase (Boehringer) as described in (18).

EXAMPLE 8

Polymerisation to duplex II (fragment F₂ of the desulphatohirudin gene)

50 pmol in each case of kinased fragment 96/67 and kinased fragment 154/64 are dissolved in 24 μl of water, the solution is heated at 90° C. for 3 minutes and cooled to 12° C. within a period of 5 minutes, After the addition of 4 μl of endo-R buffer (0.1 molar tris·HCl pH 7.5, 66 mM MgCl₂, 66 mM β-mercaptoethanol, 0.6M NaCl), 10 μl of deoxynucleoside triphosphate mixture (dATP, dCTP, dGTP, TTP, each 2×10⁻³ molar, adjusted with NH₃ to pH 7.0) and 2 μl (10 units) of DNA polymerase I, Klenow fragment (Boehringer) incubation is carried out for 30 minutes at 12° C. The reaction is stopped by heating at 90° C. for 3 minutes and the mixture is stored at −80° C. until required for further processing.

In an analogous manner the kinased fragments 1/58 and 46/64 are reacted to form duplex I (fragment F₁ of the desulphatohirudin gene).

Duplexes I and II have the following structures:

Duplex I

CTGGAATTCATGGTTGTTTACACCGACTGCACCGAATCTGGTCAGAACCTGTGCCTGTGCGAAGGTTC
GACCTTAAGTACCAACAAATGTGGCTGACGTGGCTTAGACCAGTCTTGGACACGGACACGCTTCCAAG

TAACGTTTGCGGTCAGGGTAACAAATGCATCCTGGGTTCTG
ATTGCAAACGCCAGTCCCATTGTTTACGTAGGACCCAAGAC

Duplex II

CATCCTGGGTTCTGACGGTGAAAAAAACCAGTGCGTTACCGGTGAAGGTACCCCGAAACCGCAGTCTC
GTAGGACCCAAGACTGCCACTTTTTTTGGTCACGCAATGGCCACTTCCATGGGGCTTTGGCGTCAGAG

ACAACGACGGTGACTTCGAAGAAATCCCGGAAGAATACCTGCAGTAGGATCCTG
TGTTGCTGCCACTGAAGCTTCTTTAGGGCCTTCTTATGGACGTCATCCTAGGAC the DNA 96/97 of the following structure The manufacture of the fragments F₁ and F₂ of the desulphatohirudin gene is illustrated in the following scheme 5:

5'-CATCCTGGGTTCTGACGGTGAAAAAAACCAGTGCGTTACCGGTGAAGGTACCCCGAAACCG
CAGTCT-3'

Scheme 5:
Manufacture of the fragments $F_1$ and $F_2$ of the desulphatohirudin gene and of $F_1$-$F_2$ DNA

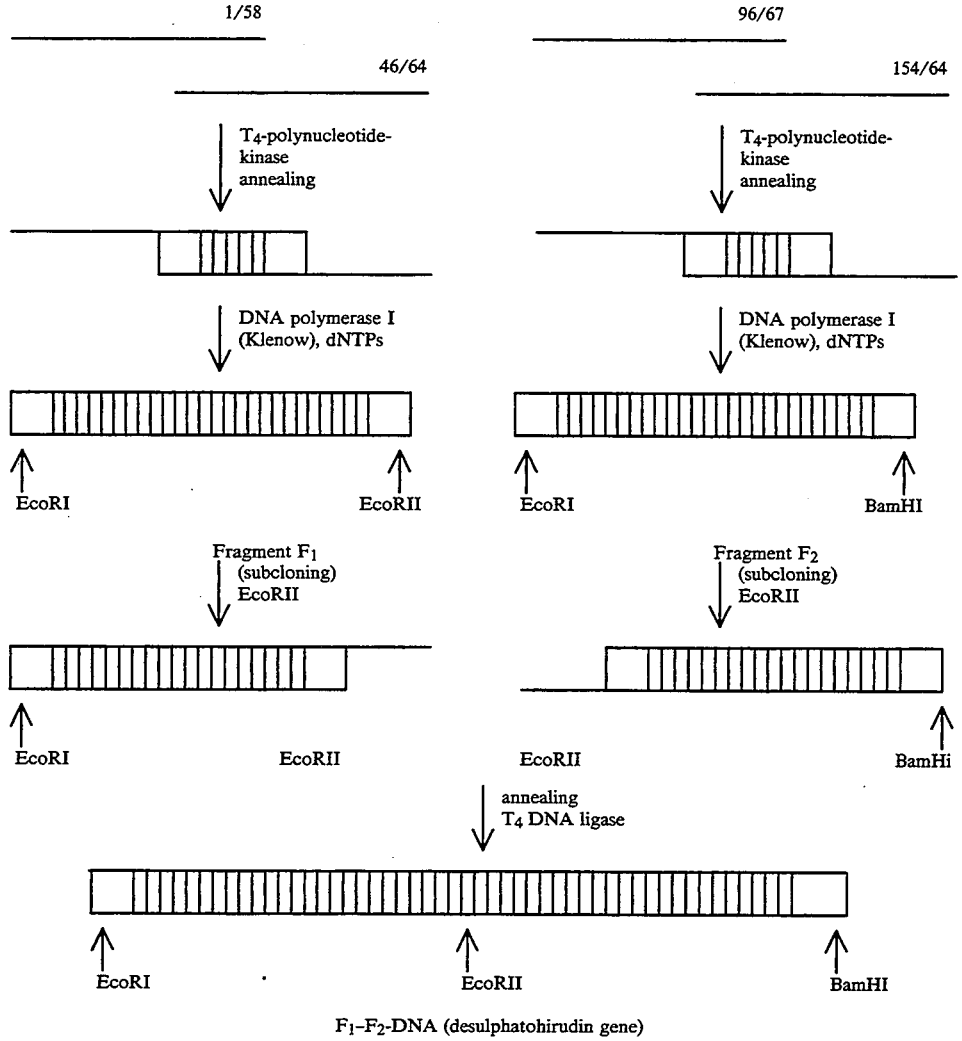

$F_1$-$F_2$-DNA (desulphatohirudin gene)

EXAMPLE 9

Polymerisation and ligation of the fragments 1/58, kinased 46/64, kinased 96/67, and 154/64; manufacture of the desulphato-hirudin gene In each case 50 pmol of fragment 1/58, kinased 46/64, kinased 96/67 and 154/64 are dissolved in 48 µl of water, the solution is heated for 3 minutes at 90° C. and cooled within 5 minutes to 12° C. After the addition of 8µl of Endo-R buffer (cf. Example 8), 20µl of deoxynucleoside triphosphate mixture (dATP, dCTP, dGTF, TTP, in each case 0.002 molar, adjusted to pH 7.0 with $NH_3$) and 2 µl (10 units) of DNA polymerase I, Klenow fragment (Boehringer) incubation is carried out for 30 minutes at 12° C. The reaction is stopped by heating from 3 minutes at 90° C. and the DNA is isolated, after extraction with phenol/chloroform, by precipitation with ethanol. The resulting DNA mixture is dissolved in 100 µl of ligase/buffer (66 mM tris·HCl pH 7.5, 6.6 mM $MgCl_2$, 10 mM dithiothreitol, 5 mM ATP), 50 units (2 µl) of $T_4$ DNA ligase (Biolabs) are added and the whole is incubated for 20 hours at 20° C. The reaction is stopped by heating for 5 minutes at 70° C. and the DNA, after extraction with phenol/chloroform, is isolated by precipitation with ethanol. After separating the mixture on an 8% polyacrylamide gel (denaturating) by electrophoresis, the ligation product with 217 base pairs is electroeluted, concentrated on a DE52 cellulose column and, after elution, isolated by precipitation with ethanol.

The desulphatohirudin gene has the following structure

```
CTGGAATTCATGGTTGTTTACACCGACTGCACCGAATCTGGTCAGAACCTGTGCCTGTGCGAAGGT
GACCTTAAGTACCAACAAATGTGGCTGACGTGGCTTAGACCAGTCTTGGACACGGACACGCTTCCA

TCTAACGTTTGCGGTCAGGGTAACAAATGCATCCTGGGTTCTGACGGTGAAAAAAACCAGTGCGTT
AGATTGCAAACGCCAGTCCCATTGTTTACGTAGGACCCAAGACTGCCACTTTTTTTGGTCACGCAA

ACCGGTGAAGGTACCCCGAAACCGCAGTCTCACAACGACGGTGACTTCGAAGAAATCCCGGAAGAA
TGGCCACTTCCATGGGGCTTTGGCGTCAGAGTGTTGCTGCCACTGAAGCTTCTTTAGGGCCTTCTT
```

```
TACCTGCAGTAGGATCCTG
ATGGACGTCATCCTAGGAC
```

The manufacture of the desulphatohirudin gene from the four fragments is illustrated in the following scheme 6:

dance with Mueller et al. (19) by DE-52 chromatography, extracted with phenol/chloroform and the DNA is precipitated with alcohol at −20° C. overnight. The

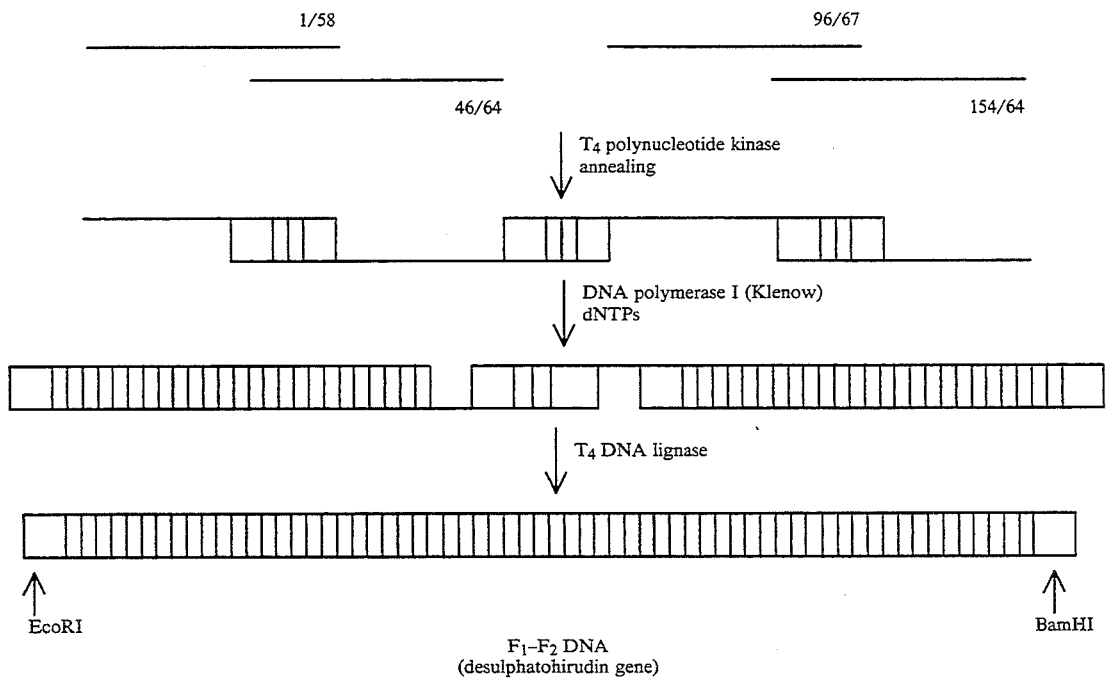

Scheme 6:
Manufacture of the hirudin gene from the four synthetic fragments $F_1$–$F_2$ DNA
(desulphatohirudin gene)

EXAMPLE 10

Manufacture of the plasmid pML 300 containing the $F_1$-DNA of the desulphatohirudin gene (FIG. 1)

a) Manufacture of the linearised vector pBR322/EcoRI/PvuII.

5 μg of pBR322 plasmid DNA are digested with 5 units of PvuII restriction endonuclease (Biolabs) in 200 ml of a solution of 100 μg/ml of gelatin for 1 hour at 37° C. Subsequently this solution is adjusted to 100 mM tris·φHCl (pH 7.5), 50 mM NaCl and the DNA is digested with 30 units of EcoRI restriction endo-nuclease (Biolabs) for 2 hours at 37° C. The solution is then adjusted to 50 mM tris-HCl pH 8 and, at a DNA concentration of 10 μg/μl, incubated with 2 units of intestinal alkaline calf phosphatase (Boehringer) for 30 mins at 37° C. The enzyme is inactivated by heating the solution for 60 minutes at 65° C. The solution is then standardised with TNE, extracted with 1 volume of phenol and chloroform, and the digested DNA is precipitated with 2 volumes of alcohol at −20° C. overnight.

The vector (pBR322/EcoRI/PvuII, 2297 base pairs) excised from the pBR322 DNA is separated from the small DNA fragment (2067 base pairs) by gel electrophoresis on 1% low-melting agarose (Biorad) in tris-acetate-EDTA buffer pH 8. After staining the DNA in the agarose gel with EtBr, the area of the gel that contains the DNA band of the pBR322/EcoRI/PvuII vector (=2297 base pairs) is cut out of the gel and liquefied for 10 minutes at 65° C. 20 volumes of TNE are added to this DNA solution, the DNA is purified in accor- DNA precipitate is dissolved in 50μl of 0.01M tris-HCl (pH 8), 0.1 mM EDTA, and stored at −20° C. until required for use. 1.4 μg (=3.2 pmol of ends) of DNA are obtained.

b) Manufacture of $F_1$-DNA/EcoRI 24 ng (=1.3 pmol of ends) of the chemically synthesised $F_1$-DNA (see Example 8) are digested with 5 units of EcoRI restriction endonuclease (Biolabs) in 50 μl of 100 mM tris·HCl (pH 7.5), 50 mM NaCl and 100 μg/ml gelatin for 30 minutes at 37° C. Subsequently, 0.06 μg (=0.14 pmol of ends) of the linearised vector pBR322/EcoRI/PvuII (Example 10a) are added to the solution The enzyme is then, by heating at 65° C. inactivated after 10 minutes, and the solution is standardised with TNE and extracted with phenol/chloroform. The DNA is precipitated with alcohol. The precipitated DNA is stored under alcohol at −20° C. until further processing.

c) Ligation of pBR322/EcoRI/PvuII vector DNA with $F_1$-DNA/EcoRI and construction of plasmid pML300

The DNA precipitate obtained in Example 10b), which contains the two mentioned DNA fragments, is dissolved in 20 μl of a solution of 50 mM tris-HCl (pH 7.8), 10 mM MgCl$_2$, 10 mM DTT, 0.5 mM ATP, and 100 μg/l gelatin and treated with 25 units/μl T$_4$ DNA ligase (Biolabs) at 15° C. for 3 hours. In this manner the recombinant plasmid pML300, which contains the $F_1$-DNA, is obtained in the solution.

d) Transformation of *E. coli* HN101 with plasmid pML300

The *E. coli* HB101 cells pretreated with calcium that are required for the transformation are produced as described by Mandel et al. (14).

The solution obtained in c), which contains the recombinant plasmid pML300, is heated at 65° C. for 10 minutes in order to inactivate the $T_4$ DNA ligase and is then cooled to 37° C. 10 μl of this reaction mixture are added to 150 μl of calcium-treated *E. coli* HB101 cells in 10 mM $MgCl_2$ and 10 mM tris·HCl (pH 7.5) in a total volume of 200 μl.

Subsequently, this mixture is cooled in ice for 30 minutes, heated for 2 minutes at 42° C. and then left to stand for 50 minutes in 1 ml of L-medium (cf. Example 18) at 37° C. The mixture is then spread out in aliquots of 0.2 ml on 5 agar plates (McConkey Agar, Difco), which contain 60 μg/ml of ampicillin (Serva). The agar plates are then maintained at 37° C. for 16~18 hours. 484 ampicillin-resistant colonies of the transformed *E. coli* HB101 are obtained.

e) Screening the colonies that contain $F_1$-DNA 470 transformed colonies (Example 10d) are pressed off onto nitrocellulose filter B85 (Schleicher and Schüll). In accordance with Grunstein and Hogness (20) the colonies are lysed and their denatured DNA is fixed on the filter. Subsequently prehybridisation of the filters is carried out in 20 ml (per filter) of 4×SET [=solution of 30 mM tris·HCl (pH 8), 150 mM NaCl, 1 mM EDTA], 0.1% (w/v) Ficoll 400 (Pharmacia), 0.5% SDS, 50 μg/ml denatured calf thymus DNA for 4 hours at 64° C. Subsequently the nitrocellulose filters are treated in 20 ml (per filter) of 5×SET (w/v) Ficoll 400, 0.2% SDS and 50 μg/ml denatured calf thymus DNA for 16 hours at 64° C. with the $32_p$ radioactively labelled probe (approximately $10^3$–$10^4$ Cerencov cpm per filter). The oligonucleotide 46/64 complementary (cf. Example 6) is used as probe.

Subsequently, the filters are washed twice in 2×SET, 0.2% SDS at room temperature, then twice in 2×SET, 0.5% SDS at 60° C. (first for 30 minutes, then for 60 minutes). The filters are then dried between 3 MM paper (Whatman) and placed at −80° C. on an X-ray film (Fuji) with an intensifying screen (Ilford) for 1–2 days.

The resulting autoradiogram shows 71 positive colonies (clones) which can be used for further processing, one of which received the designation pML300.

EXAMPLE 11

Manufacture of plasmid pML305, which contains the $F_2$-DNA of the desulphatohirudin gene (FIG. 2)

a) Manufacture of linearised vector pBR322/BamHI/NruI

5 μg of pBR322 plasmid DNA are digested with 30 units of BamHI restriction endonuclease for 30 minutes at 37° C. in a solution of 100 mM NaCl, 6 mM tris·HCl (pH 7.9), 6 mM $MgCl_2$ and 100 μg/ml gelatin. 15 units of PvuII restriction endonuclease are then added to the solution and the solution is digested for 2 hours at 37° C.

The reaction mixture is heated at 70° C. for 10 minutes in order to inactivate the enzyme. Subsequently the two DNA fragments are separated from each other by gel electrophoresis on 1% low-melting agarose in tris-acetate-EDTA buffer, pH 8. (see Example 10a).

The DNA band of the pBR322 BamHI/PvuII vector (=2672 base pairs) is cut out, liquefied, and purified in accordance with Mueller et al. (19) by DE-52 chromatography. 0.75 μg (=1.5 pmol of ends) of DNA are obtained.

b) Manufacture of $F_2$-DNA/BamHI

25 μg (=1.3 pmol of ends) of chemically synthesised $F_2$-DNA (Example 8) are digested with 16 units of BamHI restriction endonuclease (Biolabs) in 20 μl of 150 mM NaCl, 6 mM tris·HCl (pH 7.9), 6 mM $MgCl_2$ and 100 μg/ml gelatin for 30 minutes at 37° C. 60 ng (=96 nmol of ends) of the linearised vector pBR322/BamHI/PvuII (Example 11a) are then added to the solution, the whole solution is standardised with TNE and extracted with phenol/chloroform, and the DNA is precipitated with 2 volumes of alcohol. The precipitated DNA is stored under alcohol at −20° C. until required for further processing.

c) Ligation of pBR322/BamHI/PvuII vector DNA with $F_2$-DNA/BamHI and construction of plasmid pML305

The DNA precipitate obtained in Example 11b), which contains the two mentioned DNA fragments, is dissolved in 20 μl of a solution of 50 mM tris·HCl (pH 7.8), 10 mM $MgCl_2$, 10 mM DTT, 0.5 mM ATP, and 100 μg/ml gelatine and treated with 15 units/μl $T_4$DNA ligase (Biolabs) at 15° C. for 3 hours. In this manner the recombinant plasmid pML305, which contains $F_2$-DNA, is obtained in the solution.

d) Transformation of *E. coli* HB101 with plasmid pML305

The transformation of the calcium-treated *E. coli* HB101 cells is carried out as described in Example 10d). 10 μl of the reaction mixture obtained in Example 12c) are used. 313 ampicillin-resistant colonies are obtained.

e) Screening the colonies that contain $F_2$-DNA 65 transformed colonies (Example 11d) are examined for $F_2$-DNA in the manner described in Example 10e). The oligonucleotide 154/64 complementary (cf. Example 6) is used as radioactive probe. 2 positive colonies are obtained in the autoradiogram, one of which is designated pML305.

EXAMPLE 12

Characterisation of clones pML300 and pML305

The DNAs of recombinant plasmids pML300 and pML305 are isolated in accordance with Ish-Horowitz (21). The nucleotide sequences of the $F_1$-DNA and $F_2$-DNA inserts are ascertained in accordance with Maxam and Gilbert (11). For this purpose, in each case 10 μg of plasmid DNA of pML300 are cleaved with EcoRI restriction endonuclease and 10 μg of plasmid DNA of pML305 are cleaved with BamHI restriction endonuclease and the linearised DNAs are isolated by gel elution from agarose gel [cf. Example 10a)]. Subsequently the isolated DNAs are digested with alkaline phosphatase and chromatographed over DE-52 (cf. Example 11a). The DNAs are then radioactively labelled at the 5'-end with $[\gamma-^{32}P]ATP$ (specific activity 5000 Ci/mmol, Amersham) and $T_4$ polynucleotide kinase (P-L-Biochemicals).

The radioactively labelled DNAs are then cleaved with a second restriction endonuclease (EcoRII). The resulting DNA fragments are isolated by gel elution from agarose. In the case of pML300 the nucleotide sequence of $F_1$-DNA is then determined from the EcoRII-EcoRI* fragment (approximately 109 base pairs) and in the case of pML300 that of $F_2$-DNA is determined in the EcoRII-BamHI* fragment (approximately 122 base pairs).

(* indicates the DNA end that is radioactively labelled).

The nucleotide sequences that are determined for F₁-DNA and F₂-DNA are identical to those illustrated in Example 8.

EXAMPLE 13

Manufacture of expression plasmid pML310 a) Construction of linearised vector pHRi148/EcoRI/-BamHI, which contains the trp promotor-operator (FIG. 3 and FIG. 4)

A. Construction of plasmid p157

10 μg of plasmid pBRH$_{trp}$ (22) are cleaved with 50 units of EcoRI (Biolabs) for 60 minutes at 37° C. and the digestion mixture, after phenol extraction, is fractionated on a saccharose density gradient (5–23%) in 50 mM tris·HCl (pH 8.0), 1 mM EDTA in a TST41 (Kontron AG) rotor. The centrifugation lasts for 14 hours at 40,000 revs/min and 15° C. 0.3 ml fractions are collected with an ISCO gradient collector at 1 ml/min. The fractions that contain the smaller fragment are combined, the solution is standardised with TNE and precipitation is effected with 2 volumes of ethanol at −20° C. After centrifugation in an Eppendorf centrifuge, the DNA is dissolved in 100 μl of 10 mM tris·HCl pH 7.5, 0.5 mM EDTA. 5 μg of this DNA fragment are cleaved with 5 units of BglII (Biolabs) for 60 minutes at 37° C. The reaction mixture is extracted with phenol and chloroform and the DNA is incubated with 2 volumes of ethanol at −80° C. for 10 minutes; the DNA is collected by centrifugation and dissolved again in 50 μl of 50 mM tris·HCl (pH 8.0). 2 μl of this solution are removed (0.2 μg of DNA) and incubated at a DNA concentration of 10 ng/μl in 50 mM tris·HCl (pH 8.0) with 1 unit of intestinal alkaline calf phosphatase (Boehringer) for 30 minutes at 37° C. The enzyme is inactivated by heating the solution for 60 minutes at 65° C. 0.04 μg of DNA is removed and incubated 5′-terminally with 10 μCi [γ−³²P]-ATP (5000 Ci/mmol, Amersham) and 5 units of T₄ polynucleotide kinase (P-L Biochemicals) in 20 μl of reaction volume in 50 mM tris·HCl (pH 9.5), 10 mM MgCl₂, and 5 mM DTT, for 30 minutes at 37° C. The radioactive sample is mixed with the non-labelled sample (see above) and the DNA fragments are fractionated by a 5–23% saccharose density gradient in 50 mM tris·HCl (pH 8.0), 1 mM EDTA in a TST60 rotor. The centrifugation is carried out for 5 hours at 60,000 revs/min and 15° C. 0.2 ml fractions are collected. The radioactivity of each fraction is determined by measuring the Cerencov radiation and the fragments are thereby identified. The desired fractions, which contain the small DNA fragment, are combined, the DNA is precipitated with 2 volumes of ethanol and, after centrifugation, is dissolved again in 20 μl of 10 mM tris·HCl pH 7.5, 0.5 mM EDTA.

The ³²P-labelled EcoRI-BglII DNA fragment is partially cleaved with 0.2 units of TaqI (Biolabs) in 50 μl volume for 10 minutes at 37° C. The reaction mixture is adjusted to 0.2% SDS, 10% glycerin, 10 mM EDTA, 0.05% bromophenol-blue, and the DNA fragments are separated on a 6% polyacrylamide gel in tris-borate-EDTA (23). The band containing the desired EcoRI-TaqI (the largest partial fragment) is identified on the autoradiogram. This fragment (L, see FIG. 3) is extracted from the gel and purified (19) and dissolved in 10 μl of 10 mM tris·HCl pH 7.5, 1 nM EDTA.

There is used as acceptor plasmid pBR322, which is cleaved with ClaI and EcoRI: 2 μg of pBR322 are digested with 4 units of ClaI (Biolabs) in 20 μl of reaction volume for 60 minutes at 37° C. The protein is extracted with phenol and the DNA is then precipitated with 2 volumes of ethanol at −80° C. for 10 minutes. The DNA is collected by centrifugation and then digested with 10 units of EcoRI (Biolabs) for 30 minutes at 37° C. in 20μl of reaction volume. Subsequently, 2 volumes of 0.1M tris·HCl (pH 8.7) are added to the solution and the whole is incubated with 1 unit of alkaline calf phosphatase (Boehringer) at 37° C. for 30 minutes. The phosphatase is then inactivated by incubation at 65° C. for 60 minutes. 100 ng of the acceptor plasmid are incubated with 5 μl of fragment L-DNA in 15 μl of reaction volume in 10 mM MgCl₂, 20 mM tris·HCl (pH 7.8), 10 mM DTT, 0.5 mM ATP with 30 units per μl of reaction volume of T₄ DNA ligase (Biolabs) for 2 hours.

5 μl of this solution are added to a mixture that contains 150 ml of *E. coli* HB101 cells treated with calcium chloride (14) in 10 mM MgCl₂, 10 mM CaCl₂ and 10 mM tris·HCl (pH 7.5) in a total volume of 200 μl. The mixture is cooled for 20 minutes in ice, heated for 1 minute at 42° C. and incubated for 10 minutes at 20° C. 1 ml of tryptone medium [tryptone medium contains 10 g of bacto-tryptone (Difco); 1 g of yeast extract (Difco); 1 g of glucose; 8 g of NaCl and 294 mg of CaCl₂.2H₂O in 1 liter of distilled water] is added and the mixture is incubated for 30 minutes at 37° C. while agitating at 300 revs/min. The mixture is plated on two agar plates (McConkey Agar, Difco; 0.6 ml/plate), supplemented with 50 μg/ml of ampicillin (Sigma). The plates are incubated for from 12 to 17 hours at 37° C.

The plasmid DNA of 10 different colonies is isolated as follows:

The colonies are, as above, used for inoculation of 10 ml of tryptone medium supplemented by 50 μg/ml of ampicillin, in a 25 ml Erlenmeyer flask. The cultures are agitated for from 15 to 18 hours at 37° C. and 300 revs/min. The cells are harvested by centrifuging (Sorval, HS-4 rotor, 10 minutes at 4000 revs/min., 4° C.). Approximately 0.1 g of cells are obtained, and these are resuspended in 1 ml of 50 mM tris·HCl (pH 8.0). 0.25 ml of lysozyme solution [10 mg/ml in 50 mM tris·HCl (pH 8.0); lysozyme is marketed by Sigma] are added and, after incubation for 10 minutes at 0° C., 0.15 ml of 0.5 mM EDTA (pH 7.5) are added. After a further 10 minutes at 0° C., 60 μl of 2% Triton X-100 (Merck) are added. After 30 minutes at 0° C. the sample is centrifuged for 30 minutes at 15,000 revs/min and 4° C. in a Sorval SA-600 rotor. The supernatant is deproteinated with 1 vol. of phenol (saturated with TNE). The phases are separated by centrifuging (Sorval HB-4 rotor) for 10 minutes at 5000 revs/min and 4° C. The upper phase is extracted twice with 1 vol. of chloroform. Pancreatic RNAse A (Sigma; 10 mg/ml in TNE preheated for 10 minuts at 85° C.) is added until a final concentration of 25 μg/ml is reached and the mixture is incubated for 40 minutes at 37° C. The solution is then adjusted with 1M NaCl and 10% polyethylene glycol 6000 (Fluka, treated for 20 minutes at 120° C. in an autoclave) and incubated for 2 hours at −10° C. The precipitate is collected in a Sorval HB-4 rotor (20 minutes at 10,000 revs/min., 0° C.) and dissolved again in 100 μl of TNE. The DNA solution is extracted with 1 volume of phenol and the DNA is precipitated with 2 volumes of ethanol for 10 minutes at −80° C. The precipitate is collected by centrifuging in an Eppendorf centrifuge and the DNA is dissolved again in 20 μl of 10 mM tris·HCl (pH 7.5) and 0.5 mM EDTA. 8 to 10 μg of plasmid DNA are obtained from a 10 ml culture.

The plasmid DNAs are analysed after digestion with the following restriction enzymes:

In each case 0.5 μg of plasmid DNA is cleaved with HpaI (Biolabs) and with HpaI (Biolabs) and EcoRI (Biolabs) with ClaI (Biolabs) according to standard directions, in accordance with the instructions of the enzyme manufacturer. The DNAs are fractionated on a 1% agarose gel in 40 mM tris-acetate (pH 7.8), 1 mM EDTA and 0.5 μg/ml ethidium bromide. The desired plasmids contain an HpaI site and, after digesting 3 times, yield in addition to the large DNA fragment 2 smaller fragments which are larger than the small EcoRI-ClaI fragment of pBR322. One of these plasmids is designated p159 (see FIG. 3).

B. Construction of plasmid pHRi145

2 μg of p159 DNA are digested with 10 units of EcoRI (Biolabs) for 30 minutes at 37° C. The DNA is extracted with phenol, precipitated with ethanol and, after centrifugation, dissolved in 10 μl of 10 mM tris·HCl (pH 7.5), 0.5 mM EDTA. The DNA digested with EcoRI is furthermore treated with 5 units of DNA polymerase (Klenow fragment) (Boehringer) in 10 mM MgCl$_2$, 10 mM β-mercaptoethanol, 50 mM NaCl, 0.1 mM dATP (P&L Biochemicals), 0.1 mM dTTP (P&L Biochemicals) for 15 minutes at 12° C. The polymerase is then inactivated by incubation at 85° C. for 5 minutes. The reaction mixture is diluted in 20 mM tris·HCl (pH 7.8), 10 mM MgCl$_2$, 10 mM DTT, 0.5 mM ATP (Sigma) by a factor of 10 and incubated with 30 units of T$_4$ DNA ligase per μl of reaction mixture for 1 hour at 15° C.

50 ng of the DNA are transformed in *E. coli* (in the manner described above) and plated out on McConkey agar plates supplemented with 50 μg/ml ampicillin.

The plasmid DNAs of 10 different colonies are isolated in the manner described above. The plasmid DNAs are analysed by digesting with EcoRI. The desired plasmids are EcoRI-resistant. The analysis is carried out in the manner described above. One of the desired plasmids is designated Hri145 (FIG. 3).

C. Construction of plasmid pHRi148

2 μg of pHRi145-DNA are treated with 5 units of ClaI (Boehringer) for 60 minutes at 37° C., then deproteinated by means of phenol extraction. The DNA is precipitated with ethanol and then dissolved in 20 μl of 10 mM tris·HCl (pH 7.5), 0.5 mM EDTA. The projecting ends are, as described above, made up with DNA polymerase I (Klenow fragment), except that dATP and dTTP are replaced by dCTP (P&L Biochemicals) and dGTP (P&L Biochemicals). The polymerase is inactivated by incubation at 85° C. for 5 minutes. 2 volumes of 0.1M tris·HCl (pH 8.7) are added to the reaction mixture which is incubated with 0.5 units of calf phosphatase (Boehringer) for 30 minutes at 37° C. The reaction mixture is deproteinated by extraction with phenol. The DNA is precipitated with ethanol and dissolved in 8 μl of 10 mM tris·HCl (pH 7.5), 0.5 mM EDTA.

A chemically synthesised DNA linker of the formula

5′-GAATTCCATGGTACCATGGAATTC-3′ is phosphorylated at the 5′ end by incubating 8 pmol of the linker with 5 μCi [γ-$^{32}$P]-ATP (5500 Ci·mmol$^{-1}$ Amersham) in 8 μl of reaction volume that contains 0.1 mM rATP (Sigma), 50 mM tris·HCl (pH 9.5), 10 mM MgCl$_2$, 5 mM DTT and 2 units of T$_4$ polynucleotide kinase (P&L Biochemicals) for 30 minutes at 37° C. The reaction is stopped by freezing at −80° C.

The radioactively labelled linker is then treated with 1 μg of ClaI and phosphatase and ligated with pHRi145-DNA (see above) in a 20 μl reaction volume that contains 0.5 mM rATP (Sigma), 10 mM DTT (Calbiochem), 20 mM tris·HCl (pH 7.8), 1 mM MgCl$_2$ and 800 units of T$_4$ DNA ligase (Biolabs). The incubation is carried out for 2 hours at 15° C. The ligase is inactivated by incubation at 85° C. for 10 minutes. Subsequently, 2 volumes of water are added, the sodium chloride concentration is adjusted to 10 mM and 20 units of KpnI (Biolabs) are added over 30 minutes at 37° C. After extraction with phenol and chloroform, the mixture is fractionated through 0.9% low-melting agarose gel (Biorad) in 40 mM tris-acetate (pH 7.8), 1 mM EDTA and 0.5 μg/ml ethidium bromide. The band, visible by UV radiation, that demonstrates the same mobility as a marker DNA of the same size is cut out with a scalpel. The portion of gel is melted for 5 minutes at 65° C. and then cooled to 37° C. A volume of approximately 20 μl is obtained. 5 μl of this solution are removed and incubated for 12 hours at 15° C. with 400 units of T$_4$ ligase (Biolabs) in 10 μl of reaction volume, which has been adjusted to 0.5 mM ATP, 10 mM DTT, 10 mM MgCl$_2$, 20 mM tris·HCl (pH 7.8). 1/10 volume of a solution with 100 mM tris·HCl (pH 7.5), 100 mM CaCl$_2$ and 100 mM MgCl$_2$ are added to the ligase mixture (solidified at 15° C.) and the whole is incubated at 65° C. for 5 minutes. The solution is then used to transform calcium-treated *E. coli* HB101 cells in the manner described above. Plating out on McConkey Agar plates supplemented with 50 μg/ml ampicillin is carried out.

The plasmid DNAs of 10 different colonies are isolated in the manner described above, and the DNA is subjected to the following restriction enzyme analysis: In each case 0.5 μg of plasmid DNA is cleaved in succession with KpnI (Biolabs), NcoI (Biolabs) and EcoRI (Biolabs) in accordance with the instructions of the enzyme manufacturer. The cleavage products are fractionated on 1% agarose gels in 40 mM tris-acetate (pH 7.8), 1 mM EDTA, 0.5 μg/ml ethidium bromide. All plasmids exhibit one of these enzyme cleavage sites each, as desired. One is designated HRi148.

The plasmid HRi148 contains a tryptophan promoter-operator and a ribosomal binding site up to and including ATG. Hirudin and also other heterologous genes can be coupled directly by way of the EcoRI, NcoI, KpnI sites occurring once in the plasmid. Furthermore, this construction renders possible direct coupling and expressing of heterologous genes without the ATG necessary for the initiation of translation having to be present on the corresponding gene. This can easily be achieved by cleaving with NcoI and making up the projecting ends with DNA polymerase I, in the manner described, or by cleaving with KpnI and removing the projecting ends by nuclease S$_1$. The plasmid HRi148 is thus an expression plasmid with broad application.

D. Manufacture of the linearised vector pHRi148 EcoRI/BamHI

5 μg of plasmid DNA of pHRi148 are digested with the restriction endonucleases EcoRI and BamHI. The excised vector pHRi148/EcoRI/BamHI is isolated by means of density gradient centrifugation.

b) Manufacture of F$_1$-DNA/EcoRI/EcoRII and F$_2$-DNA/BamHI/EcoRII

I. Manufacture of F$_1$-DNA/EcoRI/EcoRII

5 μg of plasmid DNA of pML 300 are first digested with 10 units of EcoRI restriction endonuclease in 50 μl of a solution of 100 mM tris.HCl (pH 7.5), 50 mM NaCl and 100 μg/ml gelatine for 1 hour at 37° C. An aliquot (0.5 μg) of this linearised plasmid DNA/EcoRI is isolated by gel elution from an agarose gel (cf. Example 10a)) and radioactively labelled with [$\gamma$-$^{32}$P]ATP (cf. Example 12). The main amount of the plasmid DNA/EcoRI is then mixed with this radioactively labelled DNA, digested with EcoRII restriction endonuclease and the EcoRII-EcoRI* DNA fragment (109 base pairs) is separated by gel electrophoresis on 8% polyacrylamide. 200 μg of F$_1$-DNA/EcoRI*/EcoRII are isolated by gel elution.

II) Manufacture of F$_2$-DNA/BamHI/EcoRII

5 μg of plasmid DNA of pML 305 are cleaved with 10 units of BamHI restriction endonuclease. An aliquot (0.5 μg) of this linearised plasmid DNA/BamHI is isolated by gel elution from an agarose gel (cf. Example 10a)) and radioactively labelled with [$\gamma$-$^{32}$P] (cf. Example 12). The main amount of the plasmid DNA/BamHI is then mixed with this radioactively labelled DNA, digested with EcoRII restriction endonuclease and the EcoRII-BamHI* DNA fragment (122 base pairs) is separated by gel electrophoresis on 8% polyacrylamide. 250 μg of the F$_2$-DNA/BamHI*/EcoRII are isolated.

c) Ligation of F$_1$-DNA with F$_2$-DNA and construction of the expression plasmid pML310

10 ng (=473 nmol of ends) of F$_1$-DNA/EcoRI/EcoRII and 9 ng (=495 nmol of ends) of F$_2$-DNA/BamHI/EcoRII are treated in a volume of 20 μl with T$_4$ DNA ligase in the manner already described in Example 10c). Subsequently, the mixture is extracted with phenol/chloroform and the DNA is precipitated with alcohol. The DNA precipitate is then dissolved as described in Example 10c) and digested with EcoRI and BamHI restriction endonuclease. The solution is then standardised with TNE and 30 ng (=50 nmol of ends) of the vector DNA pHRi148/EcoRI/BamHI (cf. Example 13aD) are added. Subsequently, the solution is again extracted with phenol/chloroform and the DNA is precipitated with alcohol. The precipitated DNA mixture is treated in the manner indicated in Example 10c) with T$_4$ DNA ligase (Biolabs). In this manner there is produced in the solution a recombinant plasmid that contains as insert F$_1$-F$_2$-DNA (desulphatohirudin gene).

d) Transformation of E. coli HB101 with plasmid pML310

The transformation of E. coli HB101 cells treated with calcium is carried out in the manner described in Example 10d). 10 μl of the reaction mixture obtained in Example 13c) are used. 420 ampicillin-resistant colonies are obtained.

e) Screening the colonies that contain F$_1$-F$_2$-DNA 18 transformed colonies (Example 13d) are examined for their F$_1$-F$_2$-DNA content in the manner described in Example 10e). A mixture of the oligodeoxynucleotides described in Examples 5 and 6 is used as radioactive probe. In the autoradiogram 12 positive colonies are obtained, five of which are designated pML310, pML311, pML312, pML313, pML314.

EXAMPLE 14

Characterisation of the clone pML310

The characterisation of the F$_1$-F$_2$-DNA sequence in the recombinant plasmid pML310 is effected by sequencing the F$_1$-F$_2$-DNA according to Maxam and Gilbert (11) in the manner described in Example 12. 10 μg of plasmid DNA are examined. The nucleotide sequence of the F$_1$-F$_2$-DNA is identical to that described for the synthetic desulphatohirudin gene.

EXAMPLE 15

Manufacture of the expression plasmid pML315 a) Ligation of F$_1$-DNA with F$_2$-DNA and construction of the expression plasmid pML315

24 μg (=1.3 pmol of ends) and 26 μg (=1.3 pmol of ends) of chemically synthesised F$_1$-DNA and F$_2$-DNA, respectively, (see Example 8 and scheme I) are digested in a volume of 20 μl with 5 units of EcoRII restriction endonuclease (Biolabs) in 50 mM tris.HCl (pH 8), 5 mM MgCl$_2$, 50 mM NaCl, 1 mM DTT, 100 μg/ml gelatin for 30 minutes at 37° C. Subsequently, the mixture is extracted with phenol/chloroform and the DNA is precipitated with alcohol. The DNA precipitate is then dissolved as described in Example 10c) and treated with T$_4$ DNA ligase for 3 hours at 15° C. The mixture is then extracted with phenol/chloroform and precipitated in the manner described in Example 10b). The DNA precipitate is subsequently dissolved (cf. Example 10c)) and digested with EcoRI and BamHI restriction endonuclease for 30 minutes at 37° C. 70 ng (=0.1 pmol of ends) of the linearised vector pHRi148/EcoRI/BamHI (Example 13aD) are then added to the solution, the whole solution is standardised with TNE and extracted with phenol/chloroform and the DNA is precipitated with 2 volumes of alcohol.

The resulting DNA precipitate, which contains both DNA fragments (F$_1$-F$_2$-DNA/EcoRI/BamHI and pHRi148/EcoRI/BamHI), is dissolved in 20 μl of a solution of 50 mM tris.HCl (pH 7.8), 10 mM MgCl$_2$, 10 mM DTT, 0.5 mM ATP, 100 μg/ml gelatin and treated with 15 units/μl T$_4$ DNA ligase (Biolabs) at 15° C. for 3 hours. In this manner there is produced in the solution the recombinant plasmid pML315 which contains the F$_1$-F$_2$-DNA (=desulphatohirudin gene).

b) Transformation of E. coli HB101 with plasmid pML31 5

10 μl of the mixture containing plasmid pML315 (Example 15a) are used for the transformation of calcium-treated E. coli HB101 cells. Approximately 236 ampicillin-resistant colonies are obtained.

c) Screening the colonies that contain F$_1$-F$_2$-DNA

Transformed colonies (Example 15b) are examined for the presence of F$_1$-F$_2$-DNA in the manner indicated in Example 13e).

Five positive colonies are obtained, which are designated pML31 5 to pML31 9.

EXAMPLE 16

Manufacture of expression plasmid pML320 a. Ligation of synthetic F$_1$-F$_2$-DNA with vector DNA pHRi148/EcoRI/BamHI

20 μg of the totally synthetically produced desulphatohirudin gene (F$_1$-F$_2$-DNA, cf. Example 9) are digested in 20 μl of a solution of 50 μl of 100 mM tris.HCl (pH 7.5), 50 mM NaCl and 100 μg/ml gelatin with the restriction enzyme EcoRI and then with BamHI. The solution is standardised with TNE, whereupon 30 μg (=50 nmol of ends) of the vector DNA pHRi148/EcoRI/BamHI (cf. Example 13aD) are added. The solution is extracted with phenol/chloroform and the DNA is precipitated with alcohol. The DNA precipitate is treated with T$_4$ DNA ligase (Biolabs) in the manner indicated in Example 10c). In this manner there is produced in the solution a recombinant plasmid (pML320) which contains the $F_1-F_2$-DNA (hirudin gene) as insert.

b. Transformation of *E. coli* HB101 with plasmid pML320

The transformation of the *E. coli* HB101 cells treated with calcium is carried out as described in Example 10d). 10 μl of the reaction mixture obtained in Example 16a) are used. 173 ampicillin-resistant colonies are obtained.

c) Screening the colonies that contain $F_1-F_2$-DNA 11 transformed colonies (Example 16b)) are examined for their $F_1-F_2$-DNA content in the manner described in Example 10e). A mixture of the oligodeoxynucleotides described in Examples 5 and 6 is used as radioactive probe. 14 positive colonies are obtained in the autoradiogram. Five of these are designated pML320, pML321, pML322, pML323 and pML324.

EXAMPLE 17

Characterisation of clones pML315 and pML320

The characterisation of the $F_1-F_2$ sequences in the plasmids pML315 and pML320 is carried out by sequencing the $F_1-F_2$-DNA according to Maxam and Gilbert (11) in the manner described in Example 12. The nucleotide sequences of the DNA inserts of both plasmids are identical to those of the synthetic hirudin gene.

EXAMPLE 18

Synthesis of polypeptides with hirudin activity by means of *E. coli* cells that contain plasmids with recombinant hirudin genes Synthesis of polypeptides with hirudin activity Each of the 15 clones that contain the recombinant desulphatohirudin gene, namely

*E. coli* HB101 pML 310, *E. coli* HB101 pML 311, *E. coil* HB101 pML 312,

*E. coli* HB101 pML 313, *E. coli* HB101 pML 314, *E. coli* HB101 pML 315,

*E. coli* HB101 pML 316, *E. coli* HB101 pML 317, *E. coli* HB101 pML 318,

*E. coli* HB101 pML 319, *E. coli* HB101 pML 320, *E. coli* HB101 pHL 321,

*E. coli* HB101 pHL 322, *E. coli* HB101 pHL 323, *E. coli* HB101 pML 324 is tested for the formation of hirudin activity.

For this purpose, the above-mentioned clones are cultivated in 5 ml of L-medium overnight (16 hours) at 37° C. and 250 revs/min. L-medium is composed of the following:

| Bacto tryptones | 10 g |
| Bacto yeast extract | 5 g |
| NaCl | 5 g |
| Glucose | 5 g |
| Ampicillin | 0.1 g |

Next day, 1 ml of this overnight culture is transferred into 25 ml of M9-medium. M9-medium is composed of the following:

| $Na_2HPO_4.7H_2O$ | 13.25 g |
| $KH_2PO_4$ | 3.0 g |
| NaCl | 0.5 g |
| $NH_4Cl$ | 1.0 g |
| $CaCl_2.2H_2O$ | 0.015 g |
| $MgSO_4.7H_2O$ | 0.25 g |

-continued

| casamino acids | 2.5 g |
| vitamin $B_1$ | 0.0099 g |
| glucose | 5.0 g |
| ampicillin | 0.1 g |

Cultivation is carried out at 37° C. and 250 revs/min until the bacterial suspension has reached an optical density ($OD_{623}$) of approximately 0.9–1.0. The cells (5 ml of the growing culture) are then harvested and the bacteria are resuspended in 0.5 ml of a solution of 50 mM tris.HCl (pH 8) and 30 mM NaCl. Subsequently the suspension is adjusted to 1 mg/ml of lysozyme (Boehringer) and placed in ice for 30 minutes. By alternate freezing of the suspension in liquid nitrogen and thawing at 37° C. the bacteria are destroyed. This operation is repeated five times, then the mixture is centrifuged for 30 minutes at 16000 revs/min at 4° C. The supernatants are examined for desulphatohirudin content by adding antibodies (cf. Example 18), testing the supernatants in HPLC or measuring the inhibition of thrombin (15).

The following results are obtained:

| Bacteria extract | | desulphatohirudin formation |
|---|---|---|
| *E. coli* HB101 pML 310 | | + |
| *E. coli* HB101 pML 311 | | + |
| *E. coli* HB101 pML 312 | | + |
| *E. coli* HB101 pML 313 | | + |
| *E. coli* HB101 pML 314 | | + |
| *E. coli* HB101 pML 315 | | + |
| *E. coli* HB101 pML 316 | | + |
| *E. coli* HB101 pML 317 | | + |
| *E. coli* HB101 pML 318 | | + |
| *E. coli* HB101 pML 319 | | + |
| *E. coli* HB101 pML 320 | | + |
| *E. coli* HB101 pML 321 | | + |
| *E. coli* HB101 pML 322 | | + |
| *E. coli* HB101 pML 323 | | + |
| *E. coli* HB101 pML 324 | | + |
| *E. coli* HB101 pHRi 148 | (control) | — |
| *E. coli* HB101 pBR322 | (control) | — |
| *E. coli* HB101 | (control) | — |

EXAMPLE 19

Detection of the hirudin activity

Approximately 5–10 μl of a sample that contains polypeptides with hirudin activity (cf. Example 18) are dripped onto 1 cm² of nitrocellulose paper (NZ) (BIORAD) and dried for 30 minutes at room temperature. Subsequently, the NZ is incubated for 1 hour at 37° C. in a solution of 3% serum albumin in 0.01M tris.HCl (pH 8) and 0.9% NaCl.

The NZ is then washed in a solution of 0.01M tris.HCl (pH 8) and 0.9% NaCl for 30 minutes, the solution being changed five times. Susequently, the washed NZ is treated for 2 hours at 25° C. in a solution of 3% serum albumin in 0.01M tris.HCl (pH 8) and 0.9% NaCl that contains 2 μg/ml of antibodies (antibodies produced from rabbits or monoclonal antibodies) to hirudin. Then, the NZ is washed as described above.

The NZ is subsequently treated for 2–3 hours at 25° C. with a solution of 3% serum albumin in 0.01M tris.HCl (pH 8) and 0.9% NaCl that contains 0.2 μCi/ml of $^{125}$I-protein A (sp. activity 89.8 μCi/mg) (NEN) . The NZ is then again washed in the manner described above, dried and, in a y-counter (Multi Gramma, 1260 gamma counter, LKB, Wallace), the bound radioactivity is measured, which is a measurement for the polypeptide with hirudin activity present on the NZ.

In an alternative process, the above sample is subjected to SDS-polyacrylamide gel electrophoresis (PAGE) [cf. (24)]. The PAGE electropherogram is transferred onto NZ by electro-blotting. Subsequently, the NZ is treated in the manner described above and/or autoradiographed overnight together with an X-ray film (Fuji). Areas on the NZ that contain polypeptides with hirudin activity appear on the film as black flecks.

EXAMPLE 20

Isolation and purification of desulphatohirudin with the aid of a thrombin column a. Manufacture of the polypeptide solution for the thrombin column.

150 ml of culture liquor (obtained according to Example 18) are cooled to 4° C. and the cells are removed by centrifugation (5000 revs/min., 15 minutes, Sorvall RC 3B). The clear supernatant has no hirudin activity.

The cells are then suspended in 12 ml of lysis buffer (50 mM tris.HCl pH 8, 30 mM NaCl). 15 mg of lysozyme (Boehringer) are added to this mixture and the whole is then kept at 4° C. for 30 minutes. The cells are then destroyed by freezing in liquid nitrogen and then thawing at 37° C. four times. Subsequently, the mixture is centrifuged for 30 minutes at 16000 revs/min and 4° C. The supernatant has hirudin activity. 7.7 g of solid ammonium sulphate are then dissolved in the supernatant (15 ml). The turbid mixture is left to stand at 4° C. for 30 minutes and then centrifuged (see above). The wet sediment is dissolved in 1 ml of 0.05 mM tris.HCl pH 8 buffer and the desired polypeptide solution is obtained.

b. Purification of hirudin on a thrombin column

The thrombin column (bed volume 4 ml) is equilibrated with 0.05M tris.HCl pH 8. 5 ml portions of the polypeptide solution obtained above are applied to the column at 4° C. with a flow rate of 7 ml/hour. Washing is then carried out with 25 ml of 0.05M tris.HCl (pH 8). The first fractions contain the non-adsorbed polypeptides, which are discarded. The column is then washed with 10 ml of 1.5M benzamidine (Merck) [cf. (25)] in 0.05M tris.HCl (pH 8) and the resulting fractions are examined for hirudin activity using the thrombin test (15). The fractions that contain the polypeptides are ascertained by measuring the $OD_{280nm}$. Fractions 25 and 26 contain the hirudin activity; they are stored at $-20°$ C. or, until required for further processing, in an ice bath. The hirudin activity in fraction 25 is 20 µg/ml and in fraction 26 is 52 µg/ml. The fractions are then dialysed or desalinated on Sephadex-G25 (Pharmacia).

SDS-polyacrylamide gel electrophoresis (24) of the product indicates a molecular weight of approximately 7000–8000 Daltons and whole number multiples thereof (oligomers).

c. Manufacture of the thrombin column

Affi gel 10 (Bio Rad) is, in accordance with the manufacturer's directions, washed with cold distilled water and coupling buffer pH 8.5 (0.1M $NaHCO_3/Na_2CO_3$ solution). A 50% suspension of the gel in coupling buffer (4 ml) is transferred into a plastics tube, mixed with the same amount of thrombin solution (120 mg in 4 ml of coupling buffer) (Calbiochem) and rotated overnight at 4° C. The gel is then washed with coupling buffer. To block the active sites that are still free, the gel is treated for 3 hours at 4° C. with 0.1 ml of 1M ethanolamine-HCl (pH 8.0) per gel, then washed with phosphate-buffered sodium chloride solution containing 10 mM sodium azide per ml of gel, and maintained at 4° C. in this solution. The degree of coupling is ascertained by measuring the extinction at 280 nm and amounts to from 15 to 30 mg of hirudin per ml of gel.

4 ml of the resulting thrombin gel are used to produce the affinity column.

EXAMPLE 21

Transformation of various E. coli strains with plasmid pML310 and cultivation of the transformed host cells In a manner analogous to that described in Example 10d), the strains E. coli JA221, E. coli LM1035 and E. coli W3110Δ102 are transformed with the plasmid pML310. Transformed colonies are examined for the presence of $F_1$–$F_2$-DNA in the manner described in Example 10e). 5, 3 and 5 positive colonies, respectively, are obtained which are designated as follows:

E. coli JA221/pML310/1
E. coli JA221/pML310/2
E. coli JA221/pML310/3
E. coli JA221/pML310/4
E. coli JA221/pML310/5
E. coli LM 1035/pML310/1
E. coli LM 1035/pML310/2
E. coli LM 1035/pML310/3
E. coli W3110Δ102/pML310/1
E. coli W3110Δ102/pML310/2
E. coli W3110Δ102/pML310/3
E. coli W3110Δ102/pML310/4
E. coli W3110Δ102/pML310/5

The clones mentioned are cultivated in a modified M9-medium, which has the following composition:

| | |
|---|---|
| $Na_2HPO_4.7H_2O$ | 9.0 g |
| $KH_2PO_4$ | 3.0 g |
| NaCl | 0.5 g |
| $NH_4Cl$ | 3.5 g |
| $CaCl_2.2H_2O$ | 0.015 g |
| $MgSO_4.7H_2O$ | 0.25 g |
| casamino acids | 7.0 g |
| yeast extract | 5.0 g |
| vitamin $B_1$ | 0.0099 g |
| iron(III) citrate | 0.006 g |
| MOPS (3-morpholinopropane-l-sulphonic acid) | 34.0 g |
| glucose | 20.0 g |
| ampicillin | 0.1 g |

Cultivation is carried out at 37° C. and 180 revs/min until the bacterial suspension has reached an optical density ($OD_{623}$) of approximately 1. Then, the cells (5 ml of the growing culture) are harvested and the bacteria are resuspended in 0.5 ml of a solution of 50 mM tris.HCl (pH 8) and 30 mM NaCl. Subsequently, the suspension is adjusted to 1 mg/ml lysozyme (Boehringer) and placed in ice for 30 min. The bacteria are disintegrated by alternately freezing the suspension in liquid nitrogen and thawing at 37° C. This operation is repeated 5 times. Subsequently, the mixture is centrifuged for 30 min. at 16000 revs/min at 4° C.

All clones are examined for the formation of polypeptides with hirudin activity by measuring the inhibition of thrombin (15). Hirudin activity (300–600 ng/ml culture solution) is detected in all bacterial extracts. For example, the following hirudin activities are ascertained:

| Strain | hirudin activity (ug/l culture solution) |
|---|---|
| E. coli LM1035/pML310/1 | 300 |
| E. coli JA 221/pML310/1 | 500 |
| E. coli W3110Δ102/pML310/1 | 600 |

EXAMPLE 22

Fermentation of the transformed strain E. coli W3110Δ102/pML310/1 in a 5000 liter fermenter, and working up of the culture broth In a manner analogous to that described in Example 21, E. coli W3110Δ102/pML310/1 cells in 3000 liters of modified M9-medium are cultivated in a 5000 liter fermenter until the suspension has reached an optical density ($OD_{623}$) of approximately 10-13.

The culture broth (pH 7.4) is cooled to 10° C., and the cells are treated with an Alfa-Laval BRPX-207 desliming apparatus. The clear supernatant contains no hirudin activity and is discarded. During desliming the slime chamber is continuously partially deslimed with lysis buffer A (50 mM tris.HCl, 30 mM NaCl, adjusted with HCl to pH 8.0) and when desliming is complete the contents of the centrifuging vessel (7 l) are discharged with complete desliming with lysis buffer A. The resulting cell mass is adjusted with buffer A to 375 l and has a pH value of 7.6. After being cooled to 5°–10° C., the suspension is conveyed through a Dyno mill (type KD5) which is provided with 4.2 l of glass beads of 0.5–0.75 mm diameter. There the cells are disintegrated. The resulting suspension is adjusted with acetic acid to an acetic acid content of around 2% (v/v) and stirred overnight at 10° C. The suspension with a pH of 3.9 is deslimed by the above-described method. The clear supernatant of 300 l is concentrated to 35 l in a falling film evaporator (hourly capacity 60 l of water). The slightly turbid concentrate is centrifuged and the resulting clear supernatant is diafiltered on an ultrafiltration unit DDS=Lab 35, which is fitted with GR 81 PP membranes (surface area 2.5 m²), against 2% acetic acid or 0.02M tris.HCl pH 7.5 buffer. The final volume is 31 l.

An aliquot portion of 2 l of this clear protein solution is applied to a Sephadex G-50 F-column (KS 370 Pharmacia) with a bed volume of 96 l, the column being equilibrated with 2% acetic acid. The main fraction contained in 15 l of eluate is concentrated by means of ultrafiltration and then diafiltered against water. The resulting clear aqueous solution is lyophilised. The working up can be carried out as described in the following Examples.

EXAMPLE 23

Cultivation of the strain E. coli W3110Δ102/pML310/1 on a laboratory scale

The strain E. coli W3110Δ102/pML310/1 is incubated in shaken flasks at 37° C. and 200 revs/min for 24 hours. The medium has the following composition (g/l):

| | |
|---|---|
| Na₂HPO₄.7H₂O | 9.0 g |
| KH₂PO₄ | 3.0 |
| NaCl | 0.5 |
| CaCl₂ | 0.015 |
| MgSO₄.7H₂O | 0.25 |
| iron (III) citrate | 0.006 |
| MOPS | 40 |
| NH₄Cl | 3.5 |
| casamino acids | 7.0 |
| yeast extract | 5.0 |
| carelose (glucose) | 20 |
| ampicillin | 0.1 |

The medium has a pH value of 6.54. During cultivation an optical density ($OD_{605nm}$) of 14.9 is reached.

The cells (50 ml of the growing culture) are harvested and resuspended in 5 ml of a solution of 50 mM tris.HCl (pH 8.0) and 30 mM NaCl. Subsequently, the suspension is shaken with 5 g of cooled glass beads (diameter 0.5 mm), or by the addition of lysozyme (Boehringer), final concentration 1 mg/ml, at intervals during 30 to 45 minutes on a Multi-Tube Vortexer at high intensity. 0.5 ml of 2% acetic acid are added to 0.5 ml of the mixture which is then centrifuged at 12,000 revs/min for 20 minutes at 4° C. The supernatant solution is examined for hirudin activity (inhibition of thrombin). The thrombin-inhibition test is carried out as follows:

The test is based on the determination of the enzymatic removal of p-nitroaniline from the substrate Chromozym · TH (tosyl-glycyl-prolyl-arginine-4-nitroanilide-acetate). The p-nitroaniline formed is measured colorimetrically at 405 nm (Micro-Elisa Auto Reader, Dynatech, Kloten). The test is carried out in microtitre plates with flat bases (Costar, Serocluster, catalogue No. 3590). The reaction time is 2 hours at 37° C. in the incubation chamber. For the test, 20 μl of the solution to be determined is diluted with 30 μl of filling buffer (0.2M tris.HCl pH 7.5, 1M NaCl, 100 μg/ml bovine serum albumin), and 20 μl of enzyme solution [10 mg of lyophilised thrombin from human plasma (Boehringer) dissolved in 1 ml of bidistilled water and diluted approximately 1:400 with the above filling buffer] and 150 μof substrate solution [20 ng chromozym TH (Boehringer) dissolved in 4 ml of bidistilled water and diluted 1:15 with the above filling buffer] are added. All solutions are measured against a blank solution consisting of 70 μl of filling buffer (see above) and 150 μl of substrate solution and against an enzyme control solution consisting of 50 μl of filling buffer, 20 μl of enzyme solution and 150 μl of substrate solution. The $OD_{405nm}$ value of the enzyme control solution after 2 hours at 37° shows 100% activity and should amount to approximately 0.8±0.2. The thrombin inhibition (as a %) of the samples is calculated in accordance with the following formula:

$$\% \text{ thrombin inhibition} = 100 - \frac{100 \times OD_{405nm} \text{ of sample}}{OD_{405nm} \text{ of enzyme control solution}}$$

The supernatant solution has a thrombin inhibition of 49.7%/20 μl.

EXAMPLE 24

Purification process for enriching hirudin compounds from culture broths

In a manner analogous to that described in Example 22, the strain E. coli W3110Δ102/pML310/1 is cultivated in a fermenter. The cells are then disintegrated, centrifuged off, and the concentrated supernatant is treated with acetic acid and then ultrafiltered or dialysed. Solutions obtained in such a manner can be purified, for example, by means of ion exchange chromatography.

a) Anion exchange chromatograph on a MONO Q column (Pharmacia) for obtaining thrombin inhibiting fractions 8.5 ml of protein solution (20 mM tris.HCl pH 7.5/150 mM NaCl) are applied to the Mono Q column by means of a chromatography system produced by Pharmacia (fast protein liquid chromatography FPLC) and eluted under the following conditions: Experimental conditions: column: Mono Q, 4.6 mm×150 min. Buffer A: 20 mM tris.HCl pH 7.5; buffer B: 20 mM tris.HCl/1M NaCl. Linear salt gradient: A: elution in the course of 9 ml with 15% buffer B, increase in the course of 10.7 ml to 70% buffer B. AUFS 1.0 at 280 nm, 1 ml fractions.

In the exclusion volume (fractions 1–10) a large protein peak is separated off from the subsequently eluted hirudin compounds. In the thrombin test, fractions 17–23 exhibit a thrombin inhibition of between 20 and 100%, the main fraction (fractions 20 and 21) with 92% inhibition being eluted at a concentration of approximately 500 mM NaCl.

b) Anion exchange chromatography on a DEAE cellulose column for enriching hirudin compounds 10 ml of a dialysate is subjected to anion exchange chromatography on DE 53 (Whatman) at pH 7.5 (chromatography conditions: column 1×5 cm (10 ml). Elution buffer A: 20 mM ammonium acetate, 100 mM NaCl, pH 7.5. Elution buffer B: 20 mM ammonium acetate, 1M NaCl, pH 4.0. Linear salt gradient using 4 column volumes of each of buffer A and buffer B respectively). Hirudin compounds elute from 0.4M NaCl. This is detected by the thrombin inhibition test.

c) Desalination on P-6 DG "Desalting Gel" (Bio-Rad)

110 ml of dialysate (20 mM tris.HCl, pH 7.5, concentrated protein solution from 2.6 l of supernatant) were separated on DE 53 in a manner analogous to that described in Example 24b. Hirudin compounds elute between fractions 46 and 52 (150 ml) separately from various more quickly eluting non-active protein peaks, and are concentrated to approximately 12 ml using a rotary evaporator. The resulting clear protein solution is applied to a Biogel P-6 DG column and eluted with water.

Experimental conditions: Column 2.5×9 cm, stationary phase 45 ml Biogel P-6 DG Desalting Gel, flow rate 1.15 ml/min, 4.6 ml fractions. The salt content can be checked by measuring conductivity or by testing by means of silver nitrate (AgCl precipitation). The main activity elutes between fractions 7 and 10, this being ascertained by means of the thrombin inhibition test. Fractions 8–10 (13.5 ml) are combined, concentrated to 1 ml using a rotary evaporator, and the clear solution is applied to a Sephadex G 50 fine column (Pharmacia) with a bed volume of 160 ml, the column being equilibrated with 1% acetic acid.

d) Gel filtration on Sephadex G50 fine (Pharmacia)

Experimental conditions: column: Sephadex G50 fine (31 g), 2.5 cm×64 cm, volume 310 ml; solvent: 1% acetic acid; flow rate 43 ml/h, 3.8 ml fraction size. AUFS: 0.1 at 282 nm. Paper feed 3.0 cm/h. Detection of the eluted activity is effected by the thrombin inhibition test. The main fraction contained in 50 ml of eluate (fractions 39–52) elutes more quickly than non-active secondary components (fractions 53 to 80). The thrombin inhibition of the active fractions is between 80 and 100%.

e) Cation exchange chromatography on CM cellulose for preliminary enrichment of active lysates 10 ml of dialysate [20 mM tris.HCl, concentrate (1:20) from 200 ml of supernatant, pH 2.0 adjusted with 3 ml of 4N HCl] were separated on a cation exchanger (CM-cellulose). Hirudin compounds elute in the exclusion volume between fractions 4 and 8. Detection is effected by means of the thrombin inhibition test. Fractions 5 and 6 inhibit by 89% and 88% respectively per 20 μl eluate.

Experimental conditions: Column: 1.5×8 cm, stationary phase: 19 ml CM-cellulose (los MZ-3146). Flow rate: 43 ml/h, 3.8 ml fractions. Linear salt gradient buffer A: 20 mM $NH_4OAc$, pH 2 adjusted with 4N HCl, buffer B: 200 mM $NH_4OAc$ pH 6.5, using 5 column volumes of each, AUFS 1.0 at 282 nm.

EXAMPLE 25

Fermentation of the transformed strain E. coli W3110Δ102/pML310/1 and working up of the culture broth In a manner analogous to that described in Example 22, E. coli W3110Δ102/pML310/1 cells in 8 l of medium L are cultivated for 5 hours in a fermenter, the suspension reaching an optical density ($OD_{623}$) of approximately 5.

The cells centrifuged from the culture broth (pH 7.2) are cooled to 10° C. and disintegrated by lysozyme treatment and by repeatedly (4×) alternately freezing in liquid nitrogen and thawing to approximately 30° C. The resulting suspension (2.5 l) is diluted with 1.5% acetic acid (2.4 l) and stirred for 30 minutes at 4° C. The percipitated bacterial proteins and other cell constituents are centrifuged off for 30 minutes at 9000 revs/min at 4° C. The clear supernatant of 3.2 l is concentrated to 320 ml using a rotary evaporator (Büchi). The concentrate is dialysed overnight against 20 mM tris.HCl pH 7.5 at 4° C. and the slightly turbid dialysate is centrifuged again. The final volume is 300 ml. The clear protein solution (0.02M tris.HCl pH 7.0) is applied to a diethylaminoethylcellulose (DE53, Whatman) (20 g) column with a bed volume of 20 ml, the column being equilibrated with buffer A (buffer A: 20 mM ammonium acetate/100 mM NaCl, pH 7.5). First, washing is carried out with 1 column volume (45 ml) at constant flow (43 ml/h) and then elution is carried out with a linear salt gradient using 5 column volumes of each of buffer A and buffer B respectively (buffer B: 20 mM ammonium acetate/4M NaCl, pH 5.0). The main fraction (fractions 24–26) contained in 100 ml of eluate and active in the thrombin inhibition test is dialysed overnight at 4° C. against 20 mM tris.HCl pH 7.5 and then concentrated using a rotary evaporator at 35° C. to a final volume of 5 ml.

The resulting clear aqueous solution is applied to a Sephadex G-50 fine column (Pharmacia) with a bed volume of 160 ml, the column (2.5×64 cm Biorad) being equilibrated with 5% acetic acid. The main activity contained in 50 ml of eluate (fractions 5–7, flow 50 ml/h, 25 min./fraction) is concentrated using a rotary evaporator and then subjected to a reverse phase HPLC separation. An aliquot (500 μl) of the individual fractions is concentrated 1:10 using a "speed vac" concentrator (Savant) and examined by means of reverse phase HPLC analysis for its content of desulphatohirudin compounds. The solutions contain desulphatohirudin compounds. Fraction 6 (18 ml) contains the smallest percentage proportion of secondary components and is further purified by means of semipreparative reverse phase HPLC.

Experimental conditions: Vydac 218 TP 510 RP-HPLC column, 10×250 mm; aliquot portions of fraction 6 (200 μl concentrated 1:10) per separation; AUFS 0.5 at 220 rim; flow rate: 2 ml/min. Eluant: A: 0.1% trifluoroacetic acid, B: acetonitrile/water 8:2+0.07% trifluoroacetic acid, 1 min. 16% B, then increase in the course of 40 min. to 64% B. The resulting fractions are diluted 1:1 with water and lyophilised. The residue consists of pure desulphatohirudin compounds.

EXAMPLE 26

Analysis of the product mixture from the fermentation of *E. coli* W3110Δ102/pML310/1

The fractions active in the thrombin inhibition test obtained according to Example 25 are subjected to HPLC analysis under two different sets of conditions.

a) Experimental conditions No. 1: Nucleosil (MN) C18, 5 Um RP-HPLC column, 4.6×120 mm; 50 μl hirudin compounds per separation, att. 6.at 214 nm; flow rate 1.2 ml/min.; eluant: A: 0.1% trifluoroacetic acid, B: acetonitrile/water 8:2 with 0.07% trifluoroacetic acid, 2 min. 16% B, then increse in the course of 30 min. to 64% B. Counterpressure: 107 bars.

Fractions are taken at one minute intervals (a total of 30) and subjected to the thrombin inhibition test and the antibody test (cf. Example 19). Fractions 12-15 prove active. Furthermore, the amino acid composition, the N-terminus and the C-terminus are determined for the active hirudin compound of fraction 14. This fraction (No. 14) is in addition compared with desulphatohirudin, which is obtained in a manner analogously to that described in Example 28 by reacting natural hirudin from leeches with the enzyme arylsulphatase. The results are compiled in the following table 1:

TABLE 1

| Fraction | Retention time | Thrombin inhibition (%) | | Antibody test Δ (cpm) | |
|---|---|---|---|---|---|
| Fr 12 | 11.75 | + | | 35 | + |
| Fr 13 | 12.50 | ++ | | | + |
| Fr 14 | 12.80 | ++ | 79 | | + | 13850 |
| Fr 15 | 13.14 | + | 27 | | + | 12440 |
| Control | — | — | 9 | | — | 250 |
| desulphatohirudin | 12.8 | ++ | 86 | | + | |

Fractions of the control strain *E. coli* W3110A102 (control) are not active either in the thrombin inhibition test or in the antibody test. Such fractions are obtained by cultivating the non-transformed strain *E. coli* W3110A102 under the same conditions as those described in Example 22 and by working up the culture broth in accordance with Example 25.

b) Experimental conditions No. 2: RP-HPLC column, Vydac 218 TP 5415 4.6×150 mm; 100 μl (1:10 conc.) fraction 6 (cf. Example 25) per separation; AUFS 0.1 at 214 nm; flow rate 1.2 ml/min.; eluant: A: 0.1% trifluoroacetic acid, B: acetonitrile/water 8:2+0.07% trifluoroacetic acid. Gradient: 2 min. 16% B, then increase in the course of 3 min. to 20% B, then increase in the course of 15 min. to 25% B, then increase in the course of 27 min. to 64% B. Counterpressure 160 bar.

Fractions active in the thrombin inhibition test and in the antibody test are listed in the following Table 2. The table also contains the concentrations of NaCl in mM that are necessary for eluting the fractions from a Mono Q-column (anion exchange chromatography) (cf. Example 24a), as well as the longest wave UV absorption bands of some fractions. All fractions exhibit, in addition, a positive reaction with anti-hirudin antibodies (cf. Example 30).

TABLE 2

| Fraction No. | Retention time (min.) RP-HPLC | Thrombin-inhibition % | Antibody test Δ/cpm | FPLC | UV($\lambda_{max}$) mM NaCl | Yield μg |
|---|---|---|---|---|---|---|
| 1 | 15.63 | 97.8 ± 2 | 16,196 | 350 | 223s,274 | 4 |
| 2 | 16.83 | 91.9 ± 2 | 14,157 | 390 | 275 | 1.6 |
| 3 | 18.43 | 79.9 ± 2 | 9,257 | | | 1 |
| 4 | 19.6 | 81.7 ± 5 | 11,877 | 420 | | 1.5 |
| 5 | 20.6 | 50.4 ± 5 | 7,647 | 460 | | 1.5 |
| 6 | 21.53 | 66.1 ± 5 | 9,584 | 500 | 273 | 1.5 |
| Control | — | 0 | 508 | | | — |
| PBS-buffer | — | — | 66 | | | |
| desulphatohirudin | 15.45 | 97.3 ± 2 | 15,400 | 350 | 274 | ca. 4 |

EXAMPLE 27

Characterisation of desulphatohirudin compounds from the fermentation of the strain *E. coli* W3110A102/pML310/1

I. The hirudin compound from fraction 14 (cf. Example 26 under "Experimental conditions No. 1", Table 1) or fraction 1 (cf. Example 26 "Experimental conditions No.2", Table 2) is characterised as follows:

a) Determination of the amino acid composition

Approximately 2.5 μg of hirudin compound are hydrolysed for 24 hours with 6N HCl at 110° C. and then analysed in accordance with Chang et al. (DABS-Cl method) (reference 31). The hydrolysate has the following composition

| Amino acid | Hydrolysate | | Amino acid | Hydrolysate | |
|---|---|---|---|---|---|
| Asp | 9.8 | (9) | Ile | 1.8 | (2) |
| Thr | 4.2 | (4) | Leu | 3.9 | (4) |
| Ser | 4.4 | (4) | Tyr | 1.5 | (2) |
| Glu | 12.6 | (13) | Phe | 1 | (1) |
| Pro | 3.7 | (3) | His | 1.1 | (1) |
| Gly | 9.3 | (9) | Lys | 3.4 | (3) |
| Val | 3.5 | (4) | Met | 0 | (0) |
| Cystine | 2.2 | (3) | Total | | (65) | b) Partial sequence analysis

5 μg (750 pmol) of the hirudin compound is subjected to a conventional sequence analysis according to Edman and the N-terminal phenylthiohydantoin (PTH)-amino acids are determined by means of RP-HPLC.

Result:

| Cycle | 1 | | | | 5 | | | | 10 |
|---|---|---|---|---|---|---|---|---|---|
| Amino acid | Val | Val | Tyr | Thr | Asp | n.d. | Thr | Glu | Ser Gly |

| Cycle | 11 | | | | 15 | |
|---|---|---|---|---|---|---|
| Amino acid | Gln | Asn | Leu | n.d. | Leu | n.d. Glu |

(n.d. = not determined).

The N-terminal sequence of the biosynthetic hirudin compound examined is thus identical to that of natural hirudin (reference 1).

c) Determination of the C-terminal amino acids by means of carboxypeptidase Y degradation The time-dependent degradation of C-terminal amino acids with carboxypeptidase Y indicats as C-terminus $$-\text{Ile}-\text{Pro}-\overset{60}{\text{Glu}}-\text{Glu}-\text{Tyr}-\text{Leu}-\overset{65}{\text{Gln}}$$

The determination of the amino acids was effected with the amino acid analyser. It is shown that $Tyr^{63}$ is not sulphated (desulphatohirudin.).

The main product from the fermentation of the transformed strain E. coli W3110A102/pML310/1 is, as the structural data and the comparison with desulphatohirudin obtained from natural hirudin show, desulphatohirudin.

The structure of the remaining fermentation products is not yet completely determined. The fractions 2–6 (cf. Table 2) are defined compounds which are adequately defined by way of HPLC and FPLC data and by the UV-absorption maximum. These compounds are certainly desulphatohirudin-like compounds which differ from desulphatohirudin by a structural microheterogeneity (for example different linked S-S bridges) or by modification at the N- or C-terminus (for example N-terminal methionyl residue or N-terminally acylated, such as formylated or acetylated).

In the case of fermentation of the strains E. coli LM1035/pML310/1, E. coli JA221/pML310/1 and E. coli HB101/pML310 too, desulphatihirudin can be identified as the main product.

EXAMPLE 28

Manufacture of desulphatohirudin from natural hirudin for comparison purposes

Natural hirudin is dissolved at 2 mg/ml of buffer (0.1M ammonium acetate, pH 5,5). 100 μl of a desalinated arylsulphatase (Boehringer) solution that contains 16 μg of arylsulphatase are added to 20 μg of hirudin (10 μl solution). The whole is incubated at 25° C. and the reaction is followed by means of HPLC analysis. After 6 hours' incubation more than 90% of the hirudin is desulphated. The retention time of the desulphatohirudin formed is, under the conditions described in Example 26 ("Experimental conditions a"), 12.8 min. and, under the conditions described in Example 26 ("Experimental conditions b"), 15.45 min.

The amino acid composition, the sequence analysis by means of Edman degradation and the determination of the C-terminal amino acids by carboxypeptidase Y degradation yield the result expected for desulphatohirudin.

EXAMPLE 29

Expression of desulphatohirudin compounds in yeast (S. cerevisiae)

The expression of foreign proteins in yeast requires a defined expression system. It should contain a strong yeast-promoter, preferably an inducible yeast-promoter, and suitable transcription stop signals on a plasmid vector with which yeast cells can be transformed. The vector also contains DNA sequences, preferably yeast 2μ sequences, that guarantee extrachromosomal replication with high copy number. It should furthermore contain a selection marker for yeast, preferably the yeast LEU2 gene, and pBR322 DNA sequences with replication origin and selection marker, preferably the ampicillin resistance gene, for use in E. coli. Such vectors are suitable as so-called shuttle vectors for multiplication in E. coli and yeast.

An expression system that meets these prerequisites is described in European Patent Application No. 100,561 and illustrated with examples for efficient expression in yeast. Foreign genes are expressed from yeast under the control of the inducible PH05 promoter of acidic phosphatase. PH05 promoter, foreign gene and PH05 transcription stop are integrated in series in the yeast vector pJDB207, which also contains DNA sequences of the yeast 2μ plasmid, the yeast LEU2 gene, the ampicillin resistance gene and the E. coli replication origin.

The expression plasmid pJDB207R/PH05-HIR is manufactured as follows:

a) Isolation of the pJDB207 vector fragment;

6 μg of the plasmid pJDB207R/IF(α-3) (EP 100,561) are completely digested with the restriction endonuclease BamHI. The resulting DNA fragments (6.85 kb and 1.15 kb) are precipitated with ethanol and taken up in 400 μl of 50 mM tris.HCl pH 8.0. 4.5 units of calf intestinal phosphatase (Boehringer, Mannheim) are added. The mixture is incubated for 1 hour at 37° C., then the phosphatase is inactivated at 65° C. for 1.5 hours. The solution is adjusted to 150 mM NaCl and then applied to a DE52 (Whatman) anion exchange column (100 μl volume) which has been equilibrated beforehand with 10 mM tris.HCl pH 7.5, 150 mM NaCl, 1 mM EDTA. After a washing operation with the same buffer, the DNA is eluted with 400 μl of 1.5M NaCL, 10 mM tris.HCl pH 7.5, 1 mM EDTA and precipitated with ethanol. The large 6.85 kb BamHI fragment is separated from the small fragment on a 1.2% agarose gel in tris-borate-EDTA buffer pH 8.3.

b) Isolation of the 534 bp PHO5 promoter fragment

6 μg of the plasmid p31/R (EP 100,561) are digested with the restriction endonucleases EcoRI and BamHI. The resulting 3 DNA fragments are separated on a 1.2% agarose gel in tris-borate-EDTA buffer pH 8.3. The 534 bp BamHI-EcoRI fragment is isolated. It contains the PH05 promoter including the transcription start sites.

c) Isolation of a 206 bp DNA fragment with the sequence coding for hirudin

9 μg of the plasmid pML310 (cf. Example 13c) are completely digested with the restriction enzymes BamHI and EcoRI. The resulting two DNA fragments are separated on a 1.2% agarose gel in tris-borate-EDTA buffer pH 8.3. The 206 bp EcoRI-BamHI fragment is isolated.

d) Ligation of the DNA fragments

The three DNA fragments mentioned in section a–c (see above) are obtained from agarose gel blocks by electroelution, purified over DE52 (Whatman) anion exchangers, precipitated with ethanol and resuspended in $H_2O$.

0.1 pmol (0.45 μg) of the 6.85 kb BamHI vector fragment, 0.3 pmol (0.1 μg) of the 534 bp BamHI-EcoRI PH05 promoter fragment and 0.25 pmol (34 ng) of the 206 bp EcoRI-BamHI fragment of pML310 are ligated in 15 μl of 60 mM tris.HCl pH 7.5, 10 mM $MgCl_2$, 10 mM DTT, 1 mM ATP with 600 units of $T_4$ DNA ligase (Biolabs) at 15° C. for 16 hours.

24 transformed $amp^R$ colonies are separately cultivated in LB medium with 100 μg/ml ampicillin. Plasmid DNA is isolated in accordance with the method of Holmes et al. (32) and analysed by a HindIII/EcoRI double digestion. The appearance of an approximately 600 bp large EcoRI-HindIII fragment indicates that in the clone concerned the PH05 promoter-hirudin DNA fragment is in the correct orientation to the transcription stop signals on the vector. As expected, approximately 50% of the clones have the correct orientation of the insert. One of these clones is designated pJDB207R/PH05-HIR.

e) Transformation of *Saccharomyces cerevisiae* $GRF_{18}$

*Saccharomyces cerevisiae* strain $GRF_{18}$ (α, his3-11, his3-15, leu2-3, leu2-112, $can^R$) is transformed with the plasmid pJDB207R/PH05-HIR in accordance with the protocol of Hinnen et al. (12). Selection for transformed yeast cells is carried out on agar plates with yeast minimal medium without leucine. A transformed yeast colony is isolated and designated *Saccharomyces cerevisiae* GRF18/pJDB207R/PH05-HIR.

f) Cultivation of *S. cerevisiae* GRF18/pJDB207R/PH05-HIR

Cells of *S. cerevisiae* GRF18/pJDB207R/PH05-HIR are agitated in 20 ml of yeast minimal medium (Difco Yeast Nitrogen base without amino acids with the addition of 2% glucose and 20 mg/l L-histidine) at 30° C. and cultivated to a cell density of $3 \times 10^7$ cells/ml. The cells are washed in 0.9% NaCl and then used for inoculating 50 ml cultures in low $P_i$-minimal medium. Low $P_i$-minimal medium is prepared corresponding to the composition of Difco Yeast Nitrogen Base medium (without amino acids), but contains 0.03 g/l $KH_2PO_4$, 1 g/l KCl, and 10 g/l L-asparagine instead of $(NH_4)_2SO_4$, 2% glucose and 1 g/l L-histidine. The cultures are inoculated up to a cell density of $4 \times 10^6$ cells/ml and agitated at 30° C. for 24 hours at 200 revs/min.

g) Analysis of the product mixture from the fermentation of *S. cerevisiae* GRF18/pJDB207R/PH05-HIR The cells (cf. Example 29f) are disintegrated as usual (cf., for example, European Patent Application No. 100,561). The supernatant treated with 1.5% acetic acid is centrifuged and each 2 ml of the clear solution is dried on a "Speed Vac" concentrator and in high vacuum. The samples are dissolved individually in 100 μl of water and subjected to HPLC analysis (conditions as in Example 26a). The thrombin inhibition of the individual fractions is tested. The fraction with a retention time of 12.8 min has a thrombin inhibition of 89.6%. According to amino acid composition this fraction is desulphatohirudin.

EXAMPLE 30

Test kit with monoclonal anti-hirudin antibodies for the determination of hirudin by competitive radioimmunoassay a. Manufacture of the monoclonal anti-hirudin antibodies A) Immunisaton of mice Pure hirudin (3 mg) in lyophilised form is dissolved in a small amount of 0.1% acetic acid and then made up to 3 ml with phosphate-buffered sodium chloride solution. The pH is adjusted to 7.2. Portions of this antigen solution are mixed with identical amounts of complete Freund's adjuvant or phosphate-buffered sodium chloride solution.

Female Balb/c mice (8 weeks old, obtained from the animal farm at Sisseln, Switzerland) are injected intravenously with 100 μg of hirudin solution in buffered sodium chloride solution. Four days later the spleen is removed for fusion.

B) Manufacture of the hybridoma and antibody test

The manufacture of the hybridoma cells is carried out by fusing the obtained spleen cells with the myeloma cell line X 63-Ag.8.6.5.3 (26). $10^8$ spleen cells and $10^7$ myeloma cells are used. The fusion is carried out in the manner described in (27).

The determination of the anti-hirudin activity in the hybridoma supernatants is carried out by means of a radioimmunoassay [RIA, (28)].

C) Isolation and purification of the anti-hirudin antibodies from ascites

Balb/c mice are pretreated intraperitoneally with 0.4 ml of pristane (Carl Roth). After one week, 2 to $5 \times 10^6$ cloned hybridoma cells are injected intraperitoneally. Ascitic fluid is repeatedly taken from each mouse and frozen at $-80°$ C. The accumulated fluid is thawed and centrifuged for 30 minutes at 4° C. and 16,000 revs/min. The fat is filtered off with suction and 0.9 volume equivalents of a saturated ammonium sulphate solution is slowly added dropwise, while stirring at 0° C. to the remaining debris-free supernatant. The resulting crude immunoglobulin fraction is passed through Sephacryl G 2000 (Pharmacia) using 0.1 mM tris.HCl (pH 8.2), in accordance with the instructions of the manufacturer. Active fractions are combined and concentrated with Amicon XM50 filter (Amicon).

b. Test kit for competitive radioimmunoassay

A solution of anti-hirudin antibodies produced according to Example 30aC) is diluted with phosphate-buffered sodium chloride solution (PBS solution) to a concentration of 1 μg per 100 μl. 100 μl of this solution are incubated for 2 hours at 37° C. in small plastics tubes or on plastics microtitre plates, antibodies being non-specifically adsorbed on the plastics surface. To saturate the active sites still free on the plastics surface, after-treatment with a bovine serum albumin solution (BSA solution) is carried out.

There are added to a series of dilutions of a sample solution or of the standard solution in BSA solution in each case 50 μl of a solution of hirudin radioactively labelled with $^{125}$iodine in known manner (29) and having an activity of 10,000 cpm per 50 μl, and incubation is then carried out on the plastics surface for 2 hours at 37° C. and subsequently for 12 hours at 4° C. The small tubes or microtitre plates are washed with phosphate-buffered sodium chloride solution and the radioactivity is measured. The concentration of hirudin in the sample solution is determined by a calibration curve determined with the standard solution.

A test kit for the described radioimmunoassay contains:

2 ml of a solution of anti-hirudin antibodies from Example 30aC) with a concentration of from 1 to 10 mg per ml.

100 ml of phosphate-buffered sodium chloride solution (PBS solution)

100 ml of 0.3% bovine serum albumin and 0.1% sodium azide in PBS solution (BSA solution), 2 ml of a solution of radioactive hirudin having an activity of 200,000 cpm/ml, 2 ml of standard solution containing 100 ng/ml of hirudin, 1 ml small tubes or microtitres plates of plastics material.

EXAMPLE 31

Pharmaceutical preparation containing a desulphatohirudin compound for parenteral administration A solution containing a desulphatohirudin compound according to Example 27 is dialysed against a 0.9% NaCl solution. The concentration of the solution is then adjusted by diluting with the same NaCl solution to 0.2 mg/ml or 2 mg/ml. These solutions are sterilised by ultrafiltration (membranes with 0.22 μm pores).

The sterilised solutions can be used directly, for example for intravenous administration. Parenterally administrable solutions that contain mixtures of desulphatohirudin compounds according to Example 27 are manufactured in an analogous manner.

References

1. J. Dodt et al., FEBS Letters 165, 180 (1984)
2. P. Walsmann et al., Pharmazie 36, 653 (1981)
3. S. A. Narang, Tetrahedron 39, 3 (1983)
4. K. L. Agarwal et al., Angew. Chem. 84, 489 (1972)
5. C. B. Reese, Tetrahedron 34, 3143 (1972)
6. R. L. Letsinger and W. B. Lunsford, J. Am. Chem. Soc. 98, 3655 (1976)
7. K. Itakura et al., J. Am. Chem. Soc. 103, 706 (1981)
8. H. G. Khorana et al., J. Biol. Chem. 251, 565 (1976)
9. S. A. Narang et al., Anal. Biochem. 121, 356 (1982)
10. K. Itakura et al., J. Biol. Chem. 257, 9226 (1982)
11. A. M. Maxam and W. Gilbert, Proc. Natl. Acad. Sci. USA 74, 560 (1977); see also Meth. Enzym. 65, 499 (1980)
12. A. Hinnen et al., Proc. Natl. Acad. Sci. USA 75, 1929 (1978)
13. Anagnostopoulos et al., J. Bacteriol. 81, 741 (1961)
14. M. Mandel et al., J. Mol. Biol. 53, 159 (1970)
15. H. U. Bergmeyer (ed.), Methods of Enzymatic Analysis, Vol. II, 3rd edition, p. 314–316, Verlag Chemie, Weinheim 1983.
16. F. Markwardt et al., Thromb. Haemostasis 47, 226 (1982)
17. Köhler and Milstein, Nature 256, 495 (1975)
18. Molecular Cloning, A laboratory Manual (ed. T. Maniatis et al.), Cold Spring Harbor Lab., 1982, p. 125
19. W. Müller et al., J. Mol. Biol. 124, 343 (1978)
20. M. Grunstein and D. S. Hogness, Proc. Natl. Acad. Sci. USA 72, 3961 (1979)
21. Ish-Horowitz, in loc. cit. 18), p. 368
22. DE-OS 3 111 405 (Genentech)
23. A. C. Peacock et al., Biochemistry 6, 1818 (1967)
24. U. K. Laemmli, Nature 227, 680 (1970)
25. P. Walsmann, Pharmazie 36, 860 (1981)
26. J. F. Kearney et al., J. Immunol. 123, 1548 (1979)
27. S. Alkan et al., Mol. Immunol. 20, 203 (1983)
28. T. Chard, An Introduction to Radioimmunoassay and related Techniques, North-Holland Publ. Comp., Amsterdam 1978
29. A. E. Bolton and W. M. Hunter, Biochem. J. 133, 529 (1973)
30. J. Clarke and J. Carbon, J. Mol. Biol. 120, 517 (1978)
31. J. Y. Chang et al., Methods in Enzymology, 91, 41 (1983).
32. D. S. Holmes et al., Anal. Biochem. 114, 193 (1981).

We claim:

1. An *E. coli* expression vector comprising an expression control sequence directly linked to a DNA sequence coding for desulphatohirudin having the formula ValValTyrThrAspCysThrGluSerGlyGlnAsnLeuCysLeuCysGlu
GlySerAsnValCysGlyGlnGlyAsnLysCysIleLeuGlySerAspGly
GluLysAsnGlnCysValThrGlyGluGlyThrProLysProGlnSerHis
AsnAspGlyAspPheGluGluIleProGluGluTyrLeuGln Such that said desulphatohirudin is expressed in an *E. Coli* host cell transformed with said expression vector wherein said DNA sequence begins with a methionine condon.

2. An *E. coli* host cell which has been transformed with an expression vector according to claim 1.

3. An *E. coli* expression vector according to claim 1 wherein the DNA sequence has the sequence

```
CTGCAATTCATGGTTGTTTACACCGACTGCACCGAATCTGGTCAGAACCTGTGCCTGTGCGAAGGT
GACCTTAAGTACCAACAAATGTGGCTGACGTGGCTTAGACCAGTCTTGGACACGGACACGCTTCCA

TCTAACGTTTGCGGTCAGGGTAACAAATGCATCCTGGGTTCTGACGGTGAAAAAAACCAGTGCGTT
AGATTGCAAACGCCAGTCCCATTGTTTACGTAGGACCCAAGACTGCCACTTTTTTTGGTCACGCAA

ACCGGTGAAGGTACCCCGAAACCGCAGTCTCACAACGACGGTGACTTCGAAGAAATCCCGGAAGAA
TGGCCACTTCCATGGGGCTTTGGCGTCAGAGTGTTGCTGCCACTGAAGCTTCTTTAGGGCCTTCTT

TACCTGCAGTAGGATCCTG
ATGGACGTCATCCTAGGAC.
```

4. An *E. coli* expression vector according to claim 1, in which the expression control sequence is that of the *E. coli* tryptophan operon.

5. An expression vector according to claim 1, in which the expression control sequence is that of the yeast PHO5 gene.

6. A process for the manufacture of biologically pure desulphatohirudin having the formula ValValTyrThrAspCysThrGluSerGlyGlnAsnLeuCysLeuCysGluGlySerAsnValCys
GlyGlnGlyAsnLysCysIleLeuGlySerAspGlyGluLysAsnGlnCysValThrGlyGluGly -continued ThrProLysProGluSerHisAsnAspGlyAspPheGluGluIleProGluGluTyrLeuGln consisting essentially of the steps of:
(a) cultivating transformed *E. coli* host cells according to claim 2 in a liquid nutrient medium that contains assimilable carbon and nitrogen sources, and (b) isolating said desulfatohirudin in biologically active form.

7. Process according to claim 6 wherein a resulting salt of desulphatohirudin is converted into the free polypeptide or a resulting polypeptide is converted into a pharmaceutically acceptable salt thereof.

* * * * *